(12) United States Patent
Friedensohn et al.

(10) Patent No.: US 8,137,392 B2
(45) Date of Patent: Mar. 20, 2012

(54) CONFORMABLE THERMAL DEVICE

(75) Inventors: Joshua Friedensohn, Arlington, TX (US); Nefetari Bordain Murph, Tucker, GA (US); Roger Bradshaw Quincy, III, Cumming, GA (US); Karen McKenzie, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1260 days.

(21) Appl. No.: 11/474,079

(22) Filed: Jun. 23, 2006

(65) Prior Publication Data

US 2007/0156213 A1 Jul. 5, 2007

Related U.S. Application Data

(63) Continuation-in-part of application No. 11/303,007, filed on Dec. 15, 2005.

(51) Int. Cl.
*A61F 7/00* (2006.01)
*A61F 7/02* (2006.01)

(52) U.S. Cl. ........ 607/114; 607/108; 607/109; 607/110; 607/111; 607/112; 602/7

(58) Field of Classification Search .......... 607/96, 607/104, 108–112, 114; 602/7, 26
See application file for complete search history.

(56) References Cited

U.S. PATENT DOCUMENTS

| | | |
|---|---|---|
| 2,035,093 A | 3/1936 | Nielsen |
| 2,144,811 A | 1/1939 | Reynolds |
| 2,153,676 A | 4/1939 | Reynolds |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,901,236 A | 8/1975 | Assarsson et al. |

(Continued)

FOREIGN PATENT DOCUMENTS

DE 19545792 A1 6/1997

(Continued)

OTHER PUBLICATIONS

Search Report and Written Opinion for PCT/US2006/046496, Apr. 19, 2007.

(Continued)

*Primary Examiner* — Roy Gibson
*Assistant Examiner* — Kaitlyn Smith
(74) *Attorney, Agent, or Firm* — Dority & Manning, P.A.

(57) ABSTRACT

A chemically-activated conformable thermal device that generates heat upon activation is provided. The thermal device typically contains an oxidizable metal that is capable of undergoing an exothermic reaction in the presence of moisture and air to generate heat. Although such metals, as well as other components of the composition (e.g., carbon), are relatively inflexible and stiff, the present inventors have nevertheless discovered that one or more conformable segments may be employed to impart flexibility and conformability to the thermal device. The conformable segments are malleable so that they yield under shear stress and acquire the shape of a surface (e.g., body part) without rupturing. The conformable segments are likewise stiff or hard enough to substantially retain the desired shape during use.

21 Claims, 9 Drawing Sheets

U.S. PATENT DOCUMENTS

| | | | |
|---|---|---|---|
| 4,076,663 A | 2/1978 | Masuda et al. | |
| 4,100,324 A | 7/1978 | Anderson et al. | |
| 4,108,146 A * | 8/1978 | Golden | 607/104 |
| 4,286,082 A | 8/1981 | Tsubakimoto et al. | |
| 4,323,534 A | 4/1982 | DesMarais | |
| 4,340,563 A | 7/1982 | Appel et al. | |
| 4,341,216 A | 7/1982 | Obenour | |
| 4,366,804 A | 1/1983 | Abe | |
| 4,537,184 A * | 8/1985 | Williams, Jr. | 602/8 |
| 4,663,220 A | 5/1987 | Wisneski et al. | |
| 4,753,240 A * | 6/1988 | Sparks | 607/108 |
| 4,758,239 A | 7/1988 | Yeo et al. | |
| 4,834,738 A | 5/1989 | Kielpikowski et al. | |
| 4,854,319 A * | 8/1989 | Tobin | 607/109 |
| 4,972,832 A * | 11/1990 | Trapini et al. | 607/108 |
| 5,093,422 A | 3/1992 | Himes | |
| 5,123,411 A * | 6/1992 | Noziri | 604/113 |
| 5,179,942 A * | 1/1993 | Drulias et al. | 128/101.1 |
| 5,213,881 A | 5/1993 | Timmons et al. | |
| 5,272,236 A | 12/1993 | Lai et al. | |
| 5,278,272 A | 1/1994 | Lai et al. | |
| 5,284,703 A | 2/1994 | Everhart et al. | |
| 5,304,599 A | 4/1994 | Himes | |
| 5,316,837 A | 5/1994 | Cohen | |
| 5,332,613 A | 7/1994 | Taylor et al. | |
| 5,350,624 A | 9/1994 | Georger et al. | |
| 5,366,491 A | 11/1994 | Ingram et al. | |
| 5,371,909 A * | 12/1994 | McCarty | 5/655 |
| 5,382,400 A | 1/1995 | Pike et al. | |
| RE34,883 E * | 3/1995 | Grim | 602/13 |
| 5,418,945 A | 5/1995 | Carter et al. | |
| 5,562,604 A * | 10/1996 | Yablon et al. | 601/148 |
| 5,584,086 A * | 12/1996 | VanWinkle et al. | 5/644 |
| 5,795,439 A | 8/1998 | Euripides et al. | |
| 5,834,114 A | 11/1998 | Economy et al. | |
| 5,836,932 A | 11/1998 | Buell et al. | |
| 5,843,057 A | 12/1998 | McCormack | |
| 5,855,999 A | 1/1999 | McCormack | |
| 5,879,378 A * | 3/1999 | Usui | 607/96 |
| 5,890,486 A | 4/1999 | Mitra et al. | |
| 5,906,879 A | 5/1999 | Huntoon et al. | |
| 5,918,590 A | 7/1999 | Burkett et al. | |
| 5,932,497 A | 8/1999 | Morman et al. | |
| 5,997,981 A | 12/1999 | McCormack et al. | |
| 6,002,064 A | 12/1999 | Kobylivker et al. | |
| 6,015,764 A | 1/2000 | McCormack et al. | |
| 6,024,762 A * | 2/2000 | Gray | 607/109 |
| 6,037,281 A | 3/2000 | Mathis et al. | |
| 6,099,556 A | 8/2000 | Usui | |
| 6,111,163 A | 8/2000 | McCormack et al. | |
| 6,114,024 A | 9/2000 | Forte | |
| 6,149,934 A | 11/2000 | Krzysik et al. | |
| 6,153,209 A | 11/2000 | Vega et al. | |
| 6,197,045 B1 | 3/2001 | Carson | |
| 6,198,018 B1 | 3/2001 | Curro | |
| 6,203,810 B1 | 3/2001 | Alemany et al. | |
| 6,238,358 B1 * | 5/2001 | Philot et al. | 602/5 |
| 6,245,401 B1 | 6/2001 | Ying et al. | |
| 6,436,128 B1 | 8/2002 | Usui | |
| 6,449,788 B1 * | 9/2002 | Nichols | 5/636 |
| 6,457,195 B1 * | 10/2002 | Holste | 5/636 |
| 6,461,457 B1 | 10/2002 | Taylor et al. | |
| 6,517,906 B1 | 2/2003 | Economy et al. | |
| 6,573,212 B2 | 6/2003 | McCrae et al. | |
| 6,639,004 B2 | 10/2003 | Falat et al. | |
| 6,658,681 B2 * | 12/2003 | Britto et al. | 5/655 |
| 6,794,024 B1 | 9/2004 | Walton et al. | |
| 6,824,557 B2 | 11/2004 | Tone et al. | |
| 6,855,434 B2 | 2/2005 | Romasn-Hess et al. | |
| 6,863,682 B2 | 3/2005 | Usui | |
| 7,185,378 B2 * | 3/2007 | Smith | 5/642 |
| 7,666,156 B2 * | 2/2010 | Brown | 602/23 |
| 7,779,495 B2 * | 8/2010 | Paranjpe et al. | 5/643 |
| 2002/0121624 A1 | 9/2002 | Usui | |
| 2004/0039316 A1 * | 2/2004 | Smith | 602/6 |
| 2004/0138598 A1 | 7/2004 | Kortuem et al. | |
| 2004/0166248 A1 | 8/2004 | Hu et al. | |
| 2006/0141882 A1 | 6/2006 | Quincy, III et al. | |
| 2006/0142712 A1 | 6/2006 | Quincy, III | |
| 2006/0142828 A1 | 6/2006 | Schorr et al. | |
| 2006/0276863 A1 | 12/2006 | Kumamoto et al. | |
| 2007/0020412 A1 | 1/2007 | Kumamoto et al. | |
| 2007/0142882 A1 | 6/2007 | Quincy, III et al. | |
| 2007/0197947 A1 * | 8/2007 | Scott | 602/26 |

FOREIGN PATENT DOCUMENTS

| | | |
|---|---|---|
| EP | 0370600 A1 | 5/1990 |
| GB | 2312846 A | 1/2007 |
| WO | WO9912734 A1 | 3/1999 |
| WO | WO0040186 A1 | 7/2000 |

OTHER PUBLICATIONS

Article—*Adsorption of Gases in Multimolecular Layers*, Brunauer et al., The Journal of the American Chemical Socieity, vol. 60, Feb. 1938, pp. 309-319.

Article—*Heat-Generating Composite Material: Fe Oxidation in Fibers of a Polymer Matrix*, Babievskaya et al., Inorganic Materials, vol. 40, No. 1, 2004, pp. 35-43.

Article—*Phase Composition of the Products of Fe Oxidation in Fe + C + NaCl + $H_2O$ + $O_2$ Exothermic Mixtures*, Babievskaya et al., Inorganic Materials, vol. 38, No. 6, 2002, pp. 586-596.

Article—*Role of Activated Carbon in Chemical Interactions in the Fe—C—NaC—$H_2O$—$O_2$ Heat-Generating System*, Drobot et al., Inorganic Materials, vol. 38, No. 5, 2002, pp. 501-506.

* cited by examiner

CONFORMABLE THERMAL DEVICE

RELATED APPLICATIONS

The present application is a continuation-in-part application of U.S. application Ser. No. 11/303,007, which was filed on Dec. 15, 2005.

BACKGROUND OF THE INVENTION

Chemically activated warming devices often employ metal reactants (e.g., iron powder) that are oxidized in the presence of air and moisture. Because the oxidation reaction is exothermic and generates heat, the resulting device may provide warmth when activated. The warming device typically contains other chemical reactants to facilitate the exothermic reaction, such as activated carbon and metal halides. The activated carbon acts as a catalyst to facilitate the exothermic reaction, while the metal halide removes surface oxide films on the metal powder to allow the reaction to proceed to a sufficient extent. Unfortunately, various problems exist with conventional chemically activated warming devices. For example, the oxidizable metal and carbon components of the device are stiff and inflexible. Consequently, during use, it is often difficult to fold and conform the thermal device to a body part. As such, a need currently exists for a technique of improving the conformability and flexibility of chemically activated thermal devices.

SUMMARY OF THE INVENTION

In accordance with one embodiment of the present invention, a chemically activated thermal device is disclosed that comprises an exothermic composition and a conformable segment that is moveably constrained within the thermal device. The conformable segment is malleable and has an aspect ratio of from about 20 to about 400.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

Figure 1:
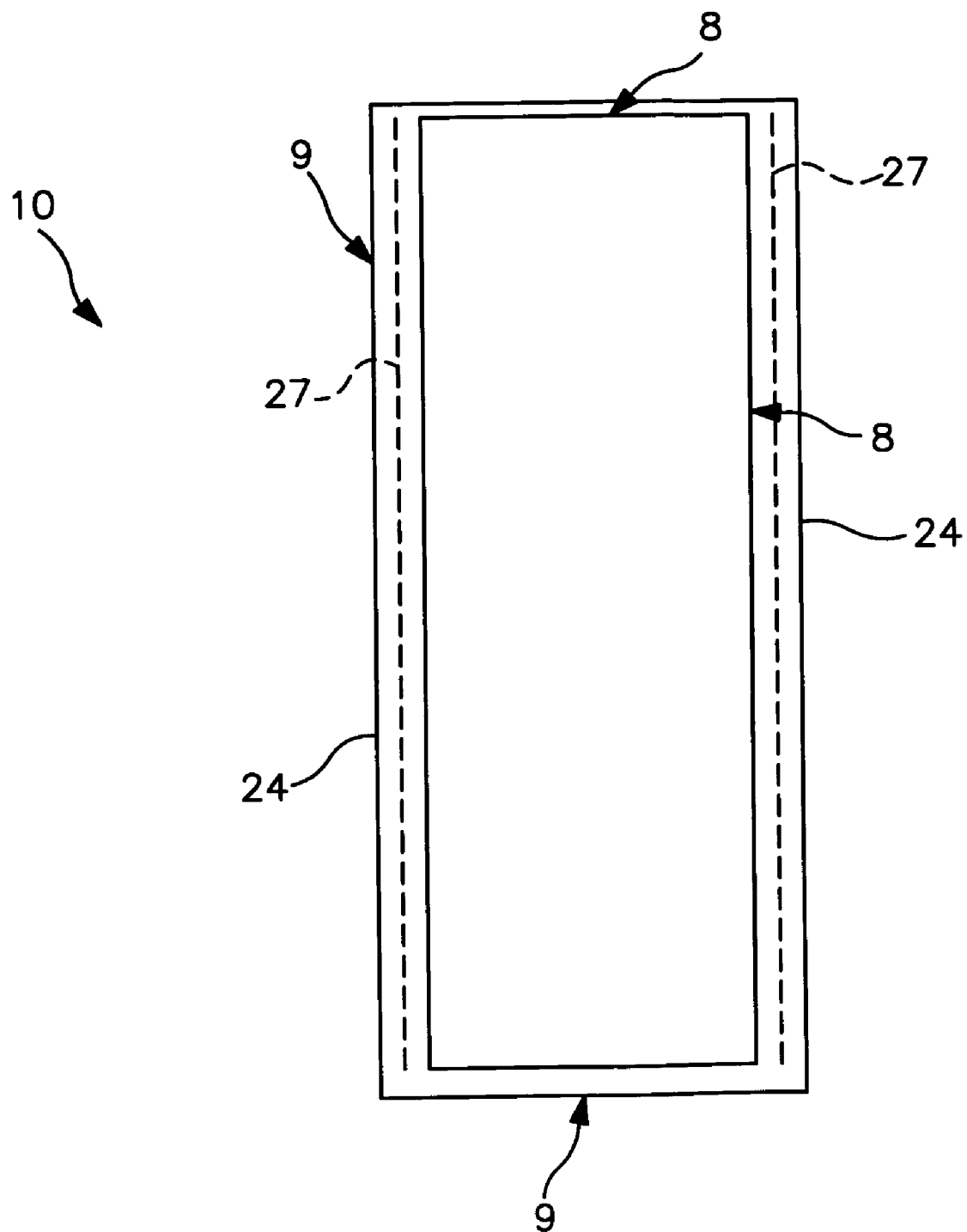
FIG. 1 illustrates a top view of one embodiment of a conformable thermal device of the present invention.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbonded fibers are generally not tacky when they are deposited onto a collecting surface. Spunbonded fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

As used herein, the "water vapor transmission rate" (WVTR) generally refers to the rate at which water vapor permeates through a material as measured in units of grams per meter squared per 24 hours (g/m$^2$/24 hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 g/m$^2$/24 hrs. Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 g/m$^2$/24 hrs. However, as is well known in the art, other systems and techniques for measuring WVTR may also be utilized.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Breathable materials may, for example, have a water vapor transmission rate (WVTR) of at least about 100 grams per square meter per 24 hours (g/m$^2$/24 hours), in some embodiments from about 500 to about 20,000 g/m$^2$/24 hours, and in some embodiments, from about 1,000 to about 15,000 g/m$^2$/24 hours.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

The present invention is directed to a conformable thermal device that generates heat upon chemical activation. The chemically activated thermal device typically contains an oxidizable metal that is capable of undergoing an exothermic reaction in the presence of moisture and air to generate heat. Although such metals, as well as other components of the composition (e.g., carbon), are relatively inflexible and stiff, the present inventors have nevertheless discovered that one or more conformable segments may be employed to impart flexibility and conformability to the thermal device. The conformable segments are malleable so that they yield under shear stress and acquire the shape of a surface (e.g., body part) without rupturing. The conformable segments are likewise stiff or hard enough to substantially retain the desired shape during use.

Although not required, the conformable segments are typically formed from a non-elastic material, such as a metal. Examples of suitable metals include aluminum, copper, zinc, tin, nickel, beryllium, iron, cesium, magnesium, manganese, silicon, sodium, etc., as well as alloys thereof. For example, the conformable segments may be formed from an alloy that contains about 50 wt. % or more aluminum, in some embodiments about 70 wt. % or more aluminum, and in some embodiments, from about 80 wt. % to about 99 wt. % aluminum. The alloy may also contain other metal components, such as silicon, iron, copper, manganese, nickel, zinc, cesium, or tin, each of which is typically present in an amount less than about 10 wt. % of the alloy. One particularly suitable aluminum alloy is a wrought alloy available from Noranda Aluminum, Inc. of New Madrid, Mo. under the designation "8176."

The shape and size of the conformable segments may be selected to enhance their ability to bend and conform to a surface. For example, the conformable segments generally have a length dimension that is substantially greater than the respective width dimension. In other words, the conformable segments possess a relatively high aspect ratio (i.e., ratio of length to width), such as from about 20 to about 400, in some embodiments from about 40 to about 200, and in some embodiments, from about 60 to about 100. The length dimension may also be selected to span about 50% or more, in some embodiments from about 75% to about 98%, and in some embodiments, from about 80% to about 95% of the length dimension of the thermal device to optimize conformability. The conformable segments may, for instance, have a length dimension ranging from about 5 to about 100 centimeters, in some embodiments from about 10 to about 50 centimeters, and in some embodiments, from about 15 to about 30 centimeters. Likewise, the width dimension of the conformable segments may range from about 0.1 to about 20 millimeters, in some embodiments from about 0.5 to about 10 millimeters, and in some embodiments, from about 1 to about 5 millimeters. Examples of such high aspect ratio segments include, without limitation, filaments, wires, strands, fibers, rods, etc.

The conformable segments may possess any desired cross-sectional shape, such as rectangular, ovular, circular, and so forth. In one embodiment, for instance, the conformable segments have a rectangular cross-sectional shape. Such rectangular segments may have a width dimension within the range noted above. Likewise, the height or thickness dimension of the rectangular segments is typically smaller than the width dimension to provide the greatest freedom of bending and lowest cost. For instance, the height dimension may range from about 0.01 to about 2 millimeters, in some embodiments from about 0.05 to about 1 millimeter, and in some embodiments, from about 0.1 to about 0.5 millimeter. Of course, the height dimension of the conformable segments need not be less than the width dimension. For circular segments, for instance, the height and width dimensions will be approximately the same.

Any number of conformable segments may be employed in the thermal device of the present invention to achieve the desired degree of conformability, such as from 2 to 100, in some embodiments from 3 to 50, and in some embodiments from 5 to 15. Regardless of the number employed, the segments generally operate cooperatively, yet independently. That is, the segments are able to move independently with respect to one another, while their mechanical characteristics are cumulative as a result of the proximity of adjacent conformable segments. The independent conformable segments may be individual members or they may be segments of a single conformable member that are connected to adjacent segments at their segment ends, such as a single wire folded back and forth across the width or along the length of the thermal device. In any case, the conformable segments may bend and move in an essentially independent manner.

The specific manner in which the conformable segments are arranged in the thermal device may also vary to improve conformability and flexibility. In one embodiment, for example, one or more conformable segments may be arranged so that their length dimension (i.e., longest dimension) is substantially parallel to the length dimension of the thermal device. In this manner, the conformable segments and thermal device may be folded, bent, or rotated about the length dimension to facilitate the flexibility of the device. Likewise, one or more conformable segments may also be positioned at or near the periphery of the thermal device. Of course, the conformable segments may be arranged or positioned at any other location of the device, such as substantially parallel to its width dimension.

Although not required, the conformable segments are typically constrained within the chemically activated thermal device to inhibit protrusion therefrom. The conforming segments may be constrained by adhesives, lamination, pressure, plastic sheathing, molding, etc. It is preferred that the chosen constraint permits some relative movement between conformable segments and the rest of the thermal device. The allowed movement reduces the stiffness of the product. To this end, the conformable segments may be incorporated into the thermal device in any of a variety of ways, depending on the manner in which the device is constructed.

The particular configuration of the thermal device is not critical to the invention. For instance, the thermal device may be a "bag-in-bag" device, which typically possesses a smaller bag containing one chemical reactant that is encompassed by a larger bag containing the other reactant. The thermal device may also be a "side-by-side" device, which uses a breakable seal positioned between two compartments, each of which contains one of the chemical reactants. These devices employ a strong exterior seal around the perimeter of the device and a weak interior seal between the two compartments. In the chemically activated thermal devices described above, the exothermic composition generally remains unattached to a substrate. In other embodiments, however, the exothermic composition may be applied or coated onto the substrate. In this regard, various embodiments of a chemically activated thermal device will now be described in more detail that employ an exothermic composition coated onto a substrate.

Figure 2:
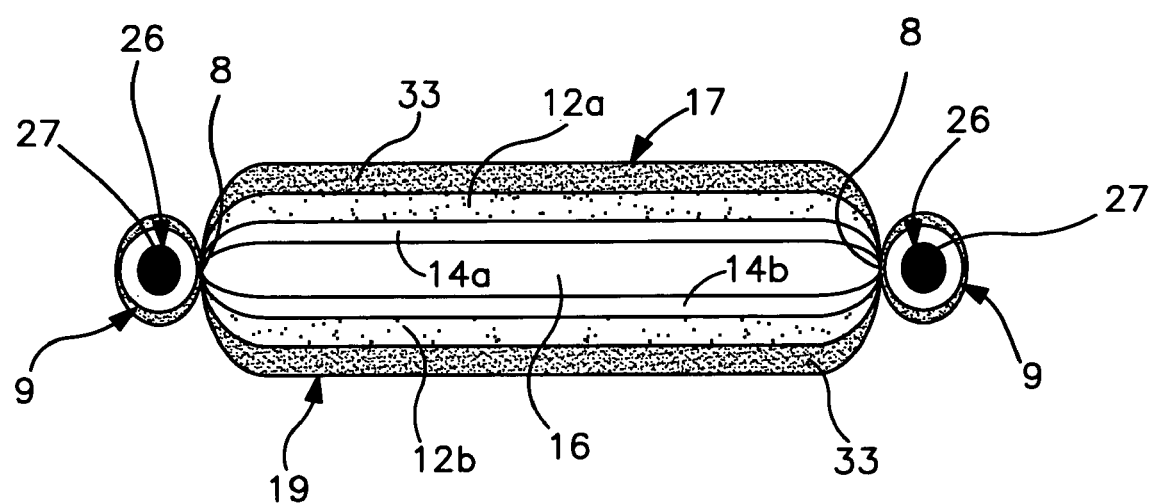
FIG. 2 illustrates a cross-sectional view of the conformable thermal device shown in FIG. 1.

Referring to FIGS. 1-2, for example, one embodiment of a chemically activated thermal device 10 will now be described in more detail. As shown, the thermal device 10 defines two outer surfaces 17 and 19, and is in the form of a substantially flat, conformable, and foldable material. The overall size and shape of the thermal device 10 are not critical. For example, the thermal device 10 may have a shape that is generally triangular, square, rectangular, pentagonal, hexagonal, circular, elliptical, etc. The thermal device 10 contains two (2) conformable segments 27, although any number of segments may of course be employed in the present invention. The conformable segments 27 are arranged so that they span approximately the entire length of the thermal device 10 to enhance its conformability properties. The conformable segments 27 are also constrained within pockets 26 located adjacent to the periphery 24 of the thermal device 10.

The pockets 26 are generally of a sufficient size and shape to allow movement of the conformable segments 27 for enhancing the flexibility of the thermal device 10. That is, the pockets 26 may have width and height dimensions greater than the respective width and height dimensions of the conformable segments 27. For example, the ratio of the width of the pockets 26 to the width of the conformable segments 27 may be from about 1.0 to about 10.0, in some embodiments, from about 1.5 to about 7.5, and in some embodiments, from about 2.0 to about 5.0. The width of the pockets 26 may, for instance, range from about 0.1 to about 200 millimeters, in some embodiments from about 1 to about 50 millimeters, and in some embodiments, from about 2 to about 25 millimeters. The ratio of the height of the pockets 26 to the height of the segments 27 may similarly fall within the above-noted ranges.

The pockets 26 may be formed by bonding together one or more layers of the thermal device 10 using any known technique, such as thermal bonding, ultrasonic bonding, adhesive bonding, stitching, etc. In the particular embodiment illustrated, for instance, the pockets 26 are formed by bonding together an outer cover 33 at regions 8 and 9. To limit access to the contents of the thermal device 10, the bond regions 9 may be located at the periphery 24 or spaced only a short distance therefrom, such as less than about 5 millimeters, and in some embodiments, less than about 2 millimeters from the periphery 24. The bond regions 8 are generally spaced apart from the bond regions 9 so that the width of the pockets 26 is large enough to accommodate the conformable segments 27. For example, the bond regions 8 may be spaced apart from the bond regions 9 by a distance of from about 1 to about 10 millimeters, in some embodiments from about 2 to about 10 millimeters, and in some embodiments, from about 3 to about 8 millimeters. In alternative embodiments, the outer cover 33 may simply be folded over at the periphery 24 to define one side of the pockets 26. In such embodiments, the bond regions 9 may or may not be employed. Of course, it should also be understood that the conformable segments 27 may be positioned at any other location of the device 10, including within or adjacent to in any other layer of the device 10.

In addition to constraining the conformable segments 27, the outer cover 33 may also provide other beneficial properties to the thermal device. For example, the outer cover 33 defines the outer surfaces 17 and 19 of the thermal device 10 and may thus present a compliant, soft feeling, and non-irritating surface to the user's skin. In this regard, the outer cover 33 may further include a composition that is configured to transfer to the wearer's skin for improving skin health, such as described in U.S. Pat. No. 6,149,934 to Krzysik et al., which is incorporated herein in its entirety by reference thereto for all purposes. The outer cover 33 may also help regulate the level of moisture and/or air that enters the thermal device 10 for activating the exothermic reaction. For example, the outer cover 33 may be formed from materials that are liquid- and vapor-permeable, liquid-impermeable and vapor-permeable ("breathable"), and so forth.

In one particular embodiment, the outer cover 33 contains a breathable film, such as a microporous or monolithic film. The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

If desired, the breathable film may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. No. 5,539,056 to Yang, et al. and U.S. Pat. No. 5,596,052 to Resconi, et al., which are incorporated herein in their entirety by reference thereto for all purposes.

If desired, blends of two or more polymers may also be utilized to form the breathable film. For example, the film may be formed from a blend of a high performance elastomer and a lower performance elastomer. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. The hysteresis value may be determined by first elongating a sample to an ultimate elongation of 50% and then allowing the sample to retract to an amount where the amount of resistance is zero. Particularly suitable high performance elastomers may include styrenic-based block copolymers, such as described above and commercially available from Kraton Polymers of Houston, Tex. under the trade designation KRATON®. Likewise, particularly suitable low performance elastomers include elastomeric polyolefins, such as metallocene-catalyzed polyolefins (e.g., single site metallocene-catalyzed linear low density polyethylene) commercially available from DuPont Dow Elastomers, LLC under the trade designation AFFINITY®. In some embodiments, the high performance elastomer may constitute from about 25 wt. % to about 90 wt. % of the polymer component of the film, and the low performance elastomer may likewise constitute from about 10 wt. % to about 75 wt. % of the polymer component of the film. Further examples of such a high performance/low performance elastomer blend are described in U.S. Pat. No. 6,794,024 to Walton, et al., which is incorporated herein in its entirety by reference thereto for all purposes.

As stated, the breathable film may be microporous. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. No. 4,341,216 to Obenour; U.S. Pat. No. 4,758,239 to Yeo, et al.; U.S. Pat. No. 5,628,737 to Dobrin, et al.; U.S. Pat. No. 5,836,932 to Buell; U.S. Pat. No. 6,114,024 to Forte; U.S. Pat. No. 6,153,209 to Vega, et al.; U.S. Pat. No. 6,198,018 to Curro; U.S. Pat. No. 6,203,810 to Alemany, et al.; and U.S. Pat. No. 6,245,401 to Ying, et al., which are incorporated herein in their entirety by reference thereto for all purposes.

If desired, the breathable film may also be bonded to a nonwoven web, knitted fabric, and/or woven fabric using well-known techniques. For instance, suitable techniques for bonding a film to a nonwoven web are described in U.S. Pat. No. 5,843,057 to McCormack; U.S. Pat. No. 5,855,999 to McCormack; U.S. Pat. No. 6,002,064 to Kobylivker, et al.; U.S. Pat. No. 6,037,281 to Mathis, et al.; and WO 99/12734, which are incorporated herein in their entirety by reference thereto for all purposes. For example, a breathable film/nonwoven laminate material may be formed from a nonwoven layer and a breathable film layer. The layers may be arranged so that the breathable film is attached to the nonwoven layer. In one particular embodiment, the outer cover 33 is formed from a nonwoven fabric (e.g., polypropylene spunbonded web) laminated to a breathable film.

Referring again to FIGS. 1-2, the thermal device 10 also includes a first thermal substrate 12a and a second thermal substrate 12b, which contain one or more exothermic compositions, such as described below. The use of multiple thermal substrates may further enhance the amount of heat generated by the thermal device. For example, the substrates may function together to provide heat to a surface, or may each provide heat to different surfaces. In addition, substrates may be employed that are not applied with the exothermic composition, but instead applied with a coating that simply facilitates the reactivity of the exothermic composition. For example, a substrate may be used near or adjacent to the thermal substrate that includes a coating of moisture-retaining particles. As described above, the moisture-retaining particles may retain and release moisture for activating the exothermic reaction. It should be understood, however, that multiple thermal substrates are not required. For instance, the thermal device may contain a single thermal substrate or none at all.

Examples of suitable thermal substrates may include, for instance, a nonwoven web, woven fabric, knit fabric, paper web, film, foam, etc. When utilized, the nonwoven web may include, but not limited to, spunbonded webs (apertured or non-apertured), meltblown webs, bonded carded webs, airlaid webs, coform webs, hydraulically entangled webs, and so forth. Typically, polymers used to form the substrate material have a softening or melting temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR™, syndiotactic polystyrene, liquid crystalline polyesters, etc.); cellulosic polymers (softwood pulp, hardwood pulp, thermomechanical pulp, etc.); combinations thereof; and so forth.

The exothermic composition may generally vary as indicated above, but is normally capable of generating heat in the presence of moisture and oxygen. For example, the exothermic composition may contain a metal that is capable of oxidizing and releasing heat. Examples of such metals include, but are not limited to, iron, zinc, aluminum, magnesium, and so forth. Although not required, the metal may be initially provided in powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method. Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic composition in an amount from about 40 wt. % to about 95 wt. %, in some embodiments from about 50 wt. % to about 90 wt. %, and in some embodiments, from about 60 wt. % to about 80 wt. %.

In addition to an oxidizable metal, a carbon component may also be utilized in the exothermic composition. Without intending to be limited in theory, it is believed that such a carbon component promotes the oxidation reaction of the metal and acts as a catalyst for generating heat. The carbon component may be activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517,906 to Economy, et al.; U.S. Pat. No. 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes.

The exothermic composition may also employ a binder for enhancing the durability of the composition when applied to a substrate. The binder may also serve as an adhesive for bonding one substrate to another substrate. Generally speaking, any of a variety of binders may be used in the exothermic composition. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the latexes typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer latexes that may be utilized in the present invention are based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer latexes described above may be readily varied, as is well known in the art, by utilizing a stabilizing agent having the desired charge during preparation of the polymer latex. Specific techniques for a carbon/polymer latex system are described in more detail in U.S. Pat. No. 6,573,212 to McCrae, et al. Activated carbon/polymer latex systems that may be used in the present invention include Nuchar® PMA, DPX-8433-68A, and DPX-8433-68B, all of which are available from MeadWestvaco Corp of Stamford, Conn.

If desired, the polymer latex may be crosslinked using any known technique in the art, such as by heating, ionization, etc. Preferably, the polymer latex is self-crosslinking in that external crosslinking agents (e.g., N-methylol acrylamide) are not required to induce crosslinking. Specifically, crosslinking agents may lead to the formation of bonds between the polymer latex and the substrate to which it is applied. Such bonding may sometimes interfere with the effectiveness of the substrate in generating heat. Thus, the polymer latex may be substantially free of crosslinking agents. Particularly suitable self-crosslinking polymer latexes are ethylene-vinyl acetate copolymers available from Celanese Corp. of Dallas, Tex. under the designation DUR-O-SET® Elite (e.g., PE-25220A). Alternatively, an inhibitor may simply be employed that reduces the extent of crosslinking, such as free radical scavengers, methyl hydroquinone, t-butylcatechol, pH control agents (e.g., potassium hydroxide), etc.

Although polymer latexes may be effectively used as binders in the present invention, such compounds sometimes result in a reduction in drapability and an increase in residual odor. Thus, water-soluble organic polymers may also be employed as binders, either alone or in conjunction with the polymer latexes, to alleviate such concerns. For example, one class of water-soluble organic polymers found to be suitable in the present invention is polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL."

The concentration of the carbon component and/or binder in the exothermic composition may generally vary based on the desired properties of the substrate. For example, the amount of the carbon component is generally tailored to facilitate the oxidation/exothermic reaction without adversely affecting other properties of the substrate. Typically, the carbon component is present in the exothermic composition in an amount about 0.01 wt. % to about 20 wt. %, in some embodiments from about 0.1 wt. % to about 15 wt. %, and in some embodiments, from about 1 wt. % to about 12 wt. %. In addition, although relatively high binder concentrations may provide better physical properties for the exothermic composition, they may likewise have an adverse effect on other properties, such as the absorptive capacity of the substrate to which it is applied. Conversely, relatively low binder concentrations may reduce the ability of the exothermic composition to remain affixed on the substrate. Thus, in most embodiments, the binder is present in the exothermic composition in an amount from about 0.01 wt. % to about 20 wt. %, in some embodiments from about 0.1 wt. % to about 10 wt. %, and in some embodiments, from about 0.5 wt. % to about 8 wt. %.

Still other components may also be employed in the exothermic composition. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic composition in an amount from about 0.01 wt. % to about 10 wt. %, in some embodiments from about 0.1 wt. % to about 8 wt. %, and in some embodiments, from about 1 wt. % to about 6 wt. %.

In addition, particles may also be employed in the exothermic composition that act as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic composition. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on substrates designed for consumer/personal use. Suitable white calcium carbonate particles are commercially available in both dry and aqueous slurry form from Omya, Inc. of Proctor, Vt. Still other suitable inorganic particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic composition in an amount from about 0.01 wt. % to about 30 wt. %, in some embodiments from about 0.1 wt. % to about 20 wt. %, and in some embodiments, from about 1 wt. % to about 15 wt. %.

In addition to the above-mentioned components, other components, such as surfactants, pH adjusters, dyes/pigments/inks, viscosity modifiers, etc., may also be included in the exothermic coating. Viscosity modifiers may be used, for example, to adjust the viscosity of the coating formulation based on the desired coating process and/or performance of the coated substrate. Suitable viscosity modifiers may include gums, such as xanthan gum. Binders, such as the cellulosic ethers, may also function as suitable viscosity modifiers. When employed, such additional components typically constitute less than about 5 wt. %, in some embodiments less than about 2 wt. %, and in some embodiments, from about 0.001 wt. % to about 1 wt. % of the exothermic coating.

To apply the exothermic composition to a substrate, the components may initially be dissolved or dispersed in a solvent. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. The concentration of the solvent is generally high enough to inhibit oxidization of the metal prior to use. Specifically, when present in a high enough concentration, the solvent may act as a barrier to prevent air from prematurely contacting the oxidizable metal. If the amount of solvent is too small, however, the exothermic reaction may occur prematurely. Likewise, if the amount of solvent is too large, the amount of metal deposited on the substrate might be too low to provide the desired exothermal effect. Although the actual concentration of solvent (e.g., water) employed will generally depend on the type of oxidizable metal and the substrate on which it is applied, it is nonetheless typically present in an amount from about 10 wt. % to about 80 wt. %, in some embodiments from about 20 wt. % to about 70 wt. %, and in some embodiments, from about 25 wt. % to about 60 wt. % of the coating formulation.

The amount of the other components added to the coating formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. % of the coating formulation. Binders may constitute from about 0.01 wt. % to about 20 wt. %, in some embodiments from about 0.1 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments, from about 1 wt. % to about 5 wt. % of the coating formulation. Further, moisture-retaining particles (e.g., calcium carbonate) may constitute from about 2 wt. % to about 30 wt. %, in some embodiments from about 3 wt. % to about 25 wt. %, and in some embodiments, from about 4 wt. % to about 10 wt. % of the coating formulation. Other components, such as surfactants, pH adjusters, viscosity modifiers, etc., may also constitute from about 0.001 wt. % to about 5 wt. %, in some embodiments from about 0.01 wt. % to about 1 wt. %, and in some embodiments from about 0.02 wt. % to about 0.5 wt. % of the coating formulation.

The solids content and/or viscosity of the coating formulation may be varied to achieve the desired amount of heat generation. For example, the coating formulation may have a solids content of from about 30% to about 80%, in some embodiments from about 40% to about 70%, and in some embodiments, from about 50% to about 60%. By varying the solids content of the coating formulation, the presence of the metal powder and other components in the exothermic composition may be controlled. For example, to form an exothermic composition with a higher level of metal powder, the coating formulation may be provided with a relatively high solids content so that a greater percentage of the metal powder is incorporated into the exothermic composition during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is less than about $2\times10^6$ centipoise, in some embodiments less than about $2\times10^5$ centipoise, in some embodiments less than about $2\times10^4$ centipoise, and in some embodiments, less than about $2\times10^3$ centipoise, such as measured with a Brookfield DV-1 viscometer with an LV spindle. If desired, thickeners or other viscosity modifiers may be employed in the coating formulation to increase or decrease viscosity.

The coating formulation may be applied to a substrate using any conventional technique, such as bar, roll, knife, curtain, print (e.g., rotogravure), spray, slot-die, drop-coating, or dip-coating techniques. The materials that form the substrate (e.g., fibers) may be coated before and/or after incorporation into the substrate. The coating may be applied to one or both surfaces of the substrate. For example, the exothermic composition may be present on a surface of the substrate that is opposite to that facing the wearer or user to avoid the possibility of burning. In addition, the coating formulation may cover an entire surface of the substrate, or may only cover a portion of the surface. When applying the exothermic composition to multiple surfaces, each surface may be coated sequentially or simultaneously.

Regardless of the manner in which the coating is applied, the resulting thermal substrate is typically heated to a certain temperature to remove the solvent and any moisture from the coating. For example, the thermal substrate may be heated to a temperature of at least about 100° C., in some embodiments at least about 110° C., and in some embodiments, at least about 120° C. In this manner, the resulting dried exothermic composition is anhydrous, i.e., generally free of water. By minimizing the amount of moisture, the exothermic composition is less likely to react prematurely and generate heat. That is, the oxidizable metal does not generally react with oxygen unless some minimum amount of water is present. Thus, the exothermic composition may remain inactive until placed in the vicinity of moisture (e.g., next to a layer that contains moisture) during use. It should be understood, however, that relatively small amounts of water may still be present in the exothermic composition without causing a substantial exothermic reaction. In some embodiments, for example, the exothermic composition contains water in an amount less than about 0.5% by weight, in some embodiments less than about 0.1% by weight, and in some embodiments, less than about 0.01% by weight.

The solids add-on level of the exothermic composition may also be varied as desired. The "solids add-on level" is determined by subtracting the weight of the untreated substrate from the weight of the treated substrate (after drying), dividing this calculated weight by the weight of the untreated substrate, and then multiplying by 100%. Lower add-on levels may optimize certain properties (e.g., absorbency), while higher add-on levels may optimize heat generation. In some embodiments, for example, the add-on level is from about 100% to about 5000%, in some embodiments from about 200% to about 2400%, and in some embodiments, from about 400% to about 1200%. The thickness of the exothermic composition may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the substrate, while still providing uniform heating.

To maintain absorbency, porosity, flexibility, and/or some other characteristic of the substrate, it may sometimes be desired to apply the exothermic composition so as to cover less than 100%, in some embodiments from about 10% to about 80%, and in some embodiments, from about 20% to about 60% of the area of one or more surfaces of the substrate. For instance, in one particular embodiment, the exothermic composition is applied to the substrate in a preselected pattern (e.g., reticular pattern, diamond-shaped grid, dots, and so forth). Although not required, such a patterned exothermic composition may provide sufficient warming to the substrate without covering a substantial portion of the surface area of the substrate. This may be desired to optimize flexibility, absorbency, or other characteristics of the substrate. It should be understood, however, that the coating may also be applied uniformly to one or more surfaces of the substrate. In addition, a patterned exothermic composition may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first exothermic composition, while another region is coated with a second exothermic composition. If desired, one region may provide a different amount of heat than another region.

Besides having functional benefits, the thermal substrate may also have various aesthetic benefits as well. For example, although containing activated carbon, the thermal substrate may be made without the black color commonly associated with activated carbon. In one embodiment, white or light-colored particles (e.g., calcium carbonate, titanium dioxide, etc.) are employed in the exothermic composition so that the resulting substrate has a grayish or bluish color. In addition, various pigments, dyes, and/or inks may be employed to alter the color of the exothermic composition. The substrate may also be applied with patterned regions of the exothermic composition to form a substrate having differently colored regions.

As indicated above, moisture and oxygen are supplied to the exothermic composition to activate the exothermic composition. To provide the desired heating profile, the rate at which moisture is allowed to contact the exothermic composition is selectively controlled. Namely, if too much moisture is supplied within a given time period, the exothermic reaction may produce an excessive amount of heat that overly warms or burns the user. On the other hand, if too little moisture is supplied within a given time period, the exothermic reaction may not be sufficiently activated. The desired application rate may of course be achieved by manually applying the desired amount of moisture, e.g., by hand or with the aid of external equipment, such as a syringe. Alternatively, the thermal device itself may contain a mechanism for controlling the moisture release rate.

Referring again to FIG. 1, one technique for using the thermal device 10 as a mechanism for controlling the moisture application rate involves, for instance, the use of a moisture-holding layer 16. It should be understood that, although shown herein as having one moisture-holding layer, any number of layers (if any) may be employed in the present invention. When employed, the moisture-holding layer 16 is configured to absorb and hold and controllably release moisture to the exothermic composition over an extended period of time. The moisture-holding layer 16 may include an absorbent web formed using any technique, such as a dry-forming technique, an airlaying technique, a carding technique, a meltblown or spunbond technique, a wet-forming technique, a foam-forming technique, etc. In an airlaying process, for example, bundles of small fibers having typical lengths ranging from about 3 to about 19 millimeters are separated and entrained in an air supply and then deposited onto a forming screen, usually with the assistance of a vacuum supply. The randomly deposited fibers then are bonded to one another using, for example, hot air or an adhesive.

The moisture-holding layer 16 typically contains cellulosic fibers, such as natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. One example of commercially available southern softwood kraft pulp fibers suitable for use in the present invention include those available from Weyerhaeuser Company with offices in Federal Way, Wash. under the trade designation of "NB-416." Another type of fluff pulp that may be used in the present invention is identified with the trade designation CR1654, available from U.S. Alliance of Childersburg, Ala., and is a bleached, highly absorbent sulfate wood pulp containing primarily softwood fibers. Still another suitable fluff pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

If desired, the moisture-holding layer 16 may also contain synthetic fibers, such as monocomponent and multicomponent (e.g., bicomponent) fibers. Multicomponent fibers, for instance, are fibers formed from at least two thermoplastic polymers that are extruded from separate extruders, but spun together to form one fiber. In a sheath/core multicomponent fiber, a first polymer component is surrounded by a second polymer component. The polymers of the multicomponent fibers are arranged in substantially constantly positioned distinct zones across the cross-section of the fiber and extend continuously along the length of the fibers. Various combinations of polymers for the multicomponent fiber may be useful in the present invention, but the first polymer component typically melts at a temperature lower than the melting temperature of the second polymer component. Melting of the first polymer component allows the fibers to form a tacky skeletal structure, which upon cooling, captures and binds many of the pulp fibers. Typically, the polymers of the multicomponent fibers are made up of different thermoplastic materials, such as polyolefin/polyester (sheath/core) bicomponent fibers in which the polyolefin (e.g., polyethylene sheath) melts at a temperature lower than the core (e.g., polyester). Exemplary thermoplastic polymers include polyolefins (e.g. polyethylene, polypropylene, polybutylene, and copolymers thereof), polytetrafluoroethylene, polyesters (e.g. polyethylene terephthalate), polyvinyl acetate, polyvinyl chloride acetate, polyvinyl butyral, acrylic resins (e.g. polyacrylate, polymethylacrylate, and polymethylmethacrylate), polyamides (e.g., nylon), polyvinyl chloride, polyvinylidene chloride, polystyrene, polyvinyl alcohol, polyurethanes, cellulosic resins (e.g., cellulosic nitrate, cellulosic acetate, cellulosic acetate butyrate, and ethyl cellulose), and copolymers of any of the above materials, such as ethylene-vinyl acetate copolymers, ethylene-acrylic acid copolymers, styrene-butadiene block copolymers, and so forth.

The moisture-holding layer 16 may also include a superabsorbent material, such as natural, synthetic and modified natural materials. Superabsorbent materials are water-swellable materials capable of absorbing at least about 20 times its weight and, in some cases, at least about 30 times its weight in an aqueous solution containing 0.9 weight percent sodium chloride. Examples of synthetic superabsorbent material polymers include the alkali metal and ammonium salts of poly(acrylic acid) and poly(methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Other suitable absorbent gelling materials are disclosed in U.S. Pat. No. 3,901,236 to Assarsson et al.; U.S. Pat. No. 4,076,663 to Masuda et al.; and U.S. Pat. No. 4,286,082 to Tsubakimoto et al., which are incorporated herein in their entirety by reference thereto for all purposes.

When utilized, the superabsorbent material may constitute from about 1 wt. % to about 40 wt. %, in some embodiments, from about 5 wt. % to about 30 wt. %, and in some embodiments, from about 10 wt. % to about 25 wt. % of the moisture-holding layer 16 (on a dry basis). Likewise, multicomponent fibers may constitute from about 1 wt. % to about 30 wt. %, in some embodiments, from about 2 wt. % to about 20 wt. %, and in some embodiments, from about 5 wt. % to about 15 wt. % of the moisture-holding layer (on a dry basis). The cellulosic fibers may also constitute up to 100 wt. %, in some embodiments from about 50 wt. % to about 95 wt. %, and in some embodiments, from about 65 wt. % to about 85 wt. % of the moisture-holding layer 16 (on a dry basis).

The evaporation rate of moisture from the moisture-holding layer 16 may be controlled to achieve the desired heating profile. By controlling the evaporation rate, the desired amount of moisture may be released to the exothermic composition within a given period of time. For example, the average "evaporation rate" of moisture from the moisture-holding layer 16 may be from about 0.05% to about 0.5%, in some embodiments from about 0.10% to about 0.25%, and in some embodiments, from about 0.15% to about 0.20% per minute. The "evaporation rate" is determined by measuring the weight of moisture-holding layer 16 at a certain time, subtracting this measured weight from the initial wet weight of the layer, dividing this value by the initial wet weight, and then multiplying by 100. The evaporation rates are calculated for several different times and then averaged. The evaporation rate may be determined at a relative humidity of 51% and temperature of about 22° C. It should be understood that these relative humidity and temperature conditions are "initial" conditions in that they may vary during testing due to the increased presence of water vapor in the atmosphere.

In some embodiments, the desired evaporation rate of moisture is achieved by controlling the nature of the aqueous solution applied to the moisture-holding layer 16. Namely, the application of only water (vapor pressure of 23.7 mm Hg at 25° C.) to the moisture-holding layer 16 may sometimes result in too great of an evaporation rate. Thus, a solute may be added to the aqueous solution to reduce its vapor pressure, i.e., the tendency of the water molecules to evaporate. At 25° C., for example, the solute may be added so that the aqueous solution added to the moisture-holding layer 16 has an evaporation rate of less than 23.7 mm Hg, in some embodiments less than about 23.2 mm Hg, and in some embodiments, from about 20.0 mm Hg to about 23.0 mm Hg. One particularly suitable class of solutes includes organic and/or inorganic metal salts. The metal salts may contain monovalent (e.g., $Na^+$), divalent (e.g., $Ca^{2+}$), and/or polyvalent cations. Examples of preferred metal cations include the cations of sodium, potassium, calcium, aluminum, iron, magnesium, zirconium, zinc, and so forth. Examples of preferred anions include halides, chlorohydrates, sulfates, citrates, nitrates, acetates, and so forth. Particular examples of suitable metal salts include sodium chloride, sodium bromide, potassium chloride, potassium bromide, calcium chloride, etc. The actual concentration of the solute in the aqueous solution may vary depending on the nature of the solute, the particular configuration of the thermal device, and the desired heating profile. For example, the solute may be present in the aqueous solution in an amount from about 0.1 wt. % to about 25 wt. %, in some embodiments from about 1 wt. % to about 20 wt. %, and in some embodiments, from about 5 wt. % to about 15 wt. % of the solution.

In addition to controlling aspects of the aqueous solution, the moisture-holding layer 16 itself may be selectively tailored to achieve the desired evaporation rate. For example, moisture-holding layers having a relatively low density and basis weight tend to release too great an amount of moisture in comparison to those having a higher density and basis weight. Without intending to be limited by theory, it is believed that such high density and high basis weight webs may have a lower porosity, thereby making it more difficult for moisture to escape from the layer over an extended period of time. Thus, in one embodiment, the moisture-holding layer 16 (e.g., airlaid web) may have a density of from about 0.01 to about 0.50, in some embodiments from about 0.05 to about 0.25, and in some embodiments, from about 0.05 to about 0.15 grams per cubic centimeters (g/cm$^3$). The density is based on the oven-dry mass of the sample and a thickness measurement made at a load of 0.34 kilopascals (kPa) with a 7.62 cm diameter circular platen at 50% relative humidity and 23° C. In addition, the basis weight of the moisture-holding layer 16 may be from about 50 to about 500 grams per square meter ("gsm"), in some embodiments from about 100 to about 300 gsm, and in some embodiments, from about 150 to about 300 gsm.

Other techniques may also be employed to achieve the desired evaporation rate of moisture from the moisture-holding layer 16. For example, superabsorbent materials are capable of swelling in the presence of an aqueous solution. Swelling increases the absorption capacity of the moisture-holding layer 16, but likewise reduces the evaporation rate of moisture as the materials exhibit a greater tendency to "hold onto" the water molecules. Thus, the evaporation rate may be increased by reducing the degree of swelling. One technique for reducing the degree of swelling of a superabsorbent material involves reducing the temperature of the aqueous solution to below ambient temperature, such as less than about 25° C., and in some embodiments, from about 5° C. to about 20° C. The degree of swelling of the superabsorbent material may also be reduced by incorporating one or more ionic compounds into the aqueous solution to increase its ionic strength. The ionic compounds may be the same as the solutes described above. The "ionic strength" of a solution may be determined according to the following equation:

$$I = 0.5 * \Sigma z_i^2 * m_i$$

wherein, $z_i$ the valence factor; and $m_i$ is the concentration. For example, the ionic strength of a solution containing 1 molar calcium chloride and 2 molar sodium chloride is "3" and determined as follows:

$$I = 0.5 * [(2^2 * 1) + (1^2 * 2)] = 3$$

Without intending to be limited by theory, it is believed that superabsorbent materials have a counterion atmosphere surrounding the ionic backbone of the polymer chains that collapses when its ionic strength is increased. Specifically, the counterion atmosphere is made up of ions of opposite charge to the charges along the backbone of a superabsorbent polymer and are present in the ionic compound (e.g., sodium or potassium cations surrounding the carboxylate anions distributed along the backbone of a polyacrylate anionic polymer). As the concentration of ions contacting the superabsorbent polymer increases, the ion concentration gradient in the liquid phase from the exterior to the interior of the polymer begins to decrease and the counterion atmosphere thickness ("Debye thickness") may be reduced from about 20 nanometers (in pure water) to about 1 nanometer or less. When the counterion atmosphere is highly extended, the counterions are more osmotically active and therefore promote a higher degree of liquid absorbency. To the contrary, when the ion concentration in the absorbed liquid increases, the counterion atmosphere collapses and the absorption capacity is diminished. As a result of the reduction in absorption capacity, the superabsorbent material exhibits less of a tendency to hold the water molecules, thereby allowing its release to the exothermic composition.

Referring again to FIGS. 1-2, breathable layers 14a and 14b may also be included within the thermal device 10 that are impermeable to liquids, but permeable to gases. This permits the flow of water vapor and air for activating the exothermic reaction, but prevents an excessive amount of liquids from contacting the thermal substrate, which could either suppress the reaction or result in an excessive amount of heat that overly warms or burns the user. The breathable layer 14a and 14b may be formed from any breathable material, such as described above. It should be understood that, although shown herein as having two breathable layers, any number of breathable layers (if any) may be employed in the present invention.

The breathable layers 14a and 14b and the moisture-holding layer 16 may be positioned in various ways relative to the thermal substrates 12a and 12b. In FIGS. 1-2, for example, the breathable layers 14a and 14b are positioned directly adjacent to respective thermal substrates 12a and 12b. As a result, the breathable layers 14a and 14b may control the amount of moisture that contacts the substrate 12a and 12b over a given period of time. The moisture-holding layer 16 may also be positioned in various locations, but is generally positioned to help facilitate the source of moisture for the thermal substrates 12a and 12b. For example, the moisture-holding layer 16 may be positioned between the thermal substrate 12a/breathable layer 14a and the thermal substrate 12b/breathable layer 14b. In this manner, the amount of moisture supplied to each substrate is relatively uniform.

Although not specifically illustrated, the thermal device 10 may also include various other layers. For example, the thermal device 10 may employ a thermally conductive layer to help distribute heat toward the direction of a user (i.e., −z direction) and/or along the x-y plane of the device 10, thereby improving the uniformity of heat application over a selected area. The thermally conductive layer may have a coefficient of thermal conductivity of at least about 0.1 Watts per meter-Kelvin (W/m-K), and in some embodiments, from about 0.1 to about 10 W/m-K. Although any thermally conductive material may generally be employed, it is often desired that the selected material be conformable to enhance the comfort and flexibility of the device 10. Suitable conformable materials include, for instance, fibrous materials (e.g., nonwoven webs), films, and so forth. Optionally, the thermally conductive layer may be gas- and/or vapor-permeable so that air may contact the thermal substrate(s) when desired to activate the exothermic reaction. One type of vapor-permeable, conformable material that may be used in the thermally conductive layer is a nonwoven web material. For example, the thermally conductive layer may contain a nonwoven laminate, such as a spunbond/meltblown/spunbond ("SMS") laminate. Such SMS laminates may also provide liquid strike-through protection and breathability. The SMS laminate is formed by well-known methods, such as described in U.S. Pat. No. 5,213,881 to Timmons, et al., which is incorporated herein its entirety by reference thereto for all purposes. Another type of vapor-permeable, conformable material that may be used in the thermally conductive layer is a breathable film. For example, the thermally conductive layer may sometimes utilize a breathable film/nonwoven laminate.

A variety of techniques may be employed to provide conductivity to the thermally conductive layer. For example, a metallic coating may be utilized to provide conductivity. Metals suitable for such a purpose include, but are not limited to, copper, silver, nickel, zinc, tin, palladium, lead, copper, aluminum, molybdenum, titanium, iron, and so forth. Metallic coatings may be formed on a material using any of a variety of known techniques, such as vacuum evaporation, electrolytic plating, etc. For instance, U.S. Pat. No. 5,656,355 to Cohen; U.S. Pat. No. 5,599,585 to Cohen; U.S. Pat. No. 5,562,994 to Abba, et al.; and U.S. Pat. No. 5,316,837 to Cohen, which are incorporated herein their entirety by reference thereto for all purposes, describes suitable techniques for depositing a metal coating onto a material. Besides a metal coating, still other techniques may be employed to provide conductivity. For example, an additive may be incorporated into the material (e.g., fibers, film, etc.) to enhance conductivity. Examples of such additives include, but are not limited to, carbon fillers, such as carbon fibers and powders; metallic fillers, such as copper powder, steel, aluminum powder, and aluminum flakes; and ceramic fillers, such as boron nitride, aluminum nitride, and aluminum oxide. Commercially available examples of suitable conductive materials include, for instance, thermally conductive compounds available from LNP Engineering Plastics, Inc. of Exton, Pa. under the name Konduit® or from Cool Polymers of Warwick, R.I. under the name CoolPoly®. Although several examples of conductive materials have been described above, it should be understood that any known thermally conductive material may be generally used in the present invention.

In addition to a thermally conductive layer, still other optional layers may be employed to enhance the effectiveness of the thermal device 10. For example, an insulation layer may be employed to inhibit heat dissipation to the outer environment so that heat is instead focused toward the patient or user. Because the insulation layer increases the overall heat-producing efficiency of the device 10, the desired temperature increase may be reached with a lower amount of exothermic coating or other reactant (i.e., moisture or oxygen). The insulation layer may have a coefficient of thermal conductivity of less than about 0.1 Watts per meter-Kelvin (W/m-K), and in some embodiments, from about 0.01 to about 0.05 W/m-k. Any known insulation material may be employed in the present invention. If desired, the selected insulation material may be fibrous in nature to improve the overall conformability of the thermal device 10. The fibrous material may possess high loft to enhance its insulative properties. Suitable high loft materials may include porous woven materials, porous nonwoven materials, etc. Particularly suitable high loft materials are nonwoven multicomponent (e.g., bicomponent) polymeric webs. For example, the multicomponent polymers of such webs may be mechanically or chemically crimped to increase loft. Examples of suitable high loft materials are described in more detail in U.S. Pat. No. 5,382,400 to Pike, et al.; U.S. Pat. No. 5,418,945 to Pike, et al. and U.S. Pat. No. 5,906,879 to Huntoon, et al., which are incorporated herein in their entirety by reference thereto for all purposes. Still other suitable materials for use as an insulation material are described in U.S. Pat. No. 6,197,045 to Carson, which is incorporated herein in its entirety by reference thereto for all purposes.

As noted above, the various layers and/or components of the thermal device 10 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In some embodiments, the exothermic composition may serve the dual purposes of generating heat and also acting as the adhesive. For example, the binder of the exothermic composition may bond together one or more layers of the thermal device 10.

Although various configurations of a thermal device have been described above, it should be understood that other configurations are also included within the scope of the present invention. For instance, other layers may also be employed to improve the exothermic properties of the thermal device. For example, a substrate may be used near or adjacent to the thermal substrate that includes a coating of moisture-retaining particles. As described above, the moisture-retaining particles may retain and release moisture for activating the exothermic reaction. Furthermore, of particular benefit, one or more of the above-mentioned layers may accomplish multiple functions of the thermal device. For example, in some embodiments, the breathable layer, moisture-holding layer, etc., may be coated with an exothermic composition and thus also serve as a thermal substrate. Although not expressly set forth herein, it should be understood that numerous other possible combinations and configurations would be well within the ordinary skill of those in the art.

Moisture may be applied any time prior to or during use of the thermal device, such as just prior to use or during manufacture. For example, water may be pre-applied to the moisture-holding layer as described above. The moisture is added in an amount effective to activate an exothermic, electrochemical reaction between the electrochemically oxidizable element (e.g., metal powder) and the electrochemically reducible element (e.g., oxygen). Although this amount may vary depending on the reaction conditions and the amount of heat desired, the moisture is typically added in an amount from about 20 wt. % to about 500 wt. %, and in some embodiments, from about 50 wt. % to about 200 wt. %, of the weight of the amount of oxidizable metal present in the coating. Although not necessarily required, it may be desired to seal such water-treated thermal devices within a substantially liquid-impermeable material (vapor-permeable or vapor-impermeable) that inhibits the exothermic composition from contacting enough oxygen to prematurely activate the exothermic reaction. To generate heat, the thermal device is simply removed from the package and exposed to air.

Certain aspects of the thermal device may be optimized to supply a controlled amount of moisture and/or oxygen to the exothermic composition during use. Through selective control over the supply of these reactants, a heating profile may be achieved in which an elevated temperature is reached quickly and maintained over an extended period of time. For example, an elevated temperature of from about 30° C. to about 60° C., in some embodiments from about 35° C. to about 55° C., and in some embodiments from about 37° C. to about 43° C., may be achieved in 20 minutes or less, and in some embodiments, 10 minutes or less. This elevated temperature may be substantially maintained for at least about 1 hour, in some embodiments at least about 2 hours, in some embodiments at least about 4 hours, and in some embodiments, at least about 10 hours (e.g., for overnight use).

The thermal device of the present invention may be employed in a wide range of articles to provide a warming effect. For example, the thermal device may be used as a heating pad, bandage, food warmer, animal warmer, water warmer, and so forth. The thermal device may also be used to deliver warmth in various other applications, such as drapes or blankets for warming patients during surgical or medical procedures.

The present invention may be better understood with reference to the following examples.

EXAMPLE 1

The ability to form a thermal device was demonstrated. Initially, pieces (7 inches by 12.5 inches) of a bonded carded web fabric were provided that had a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 400 mL pyrex beaker, 5.0 grams of METOLOSE SM-100 (Shin-Etsu Chemical Co., Ltd.) and 12.5 grams of sodium chloride (Mallinckrodt) were added to 150.0 grams of distilled water that was stirred and heated to 69° C. The mixture was stirred and allowed to cool as the following additional ingredients were added sequentially: 17.3 grams of DUR-O-SET® Elite PE 25-220A ethylene-vinyl acetate emulsion (Celanese Emulsions), 39.7 grams of XC4900 sample #04.1919704 calcium carbonate slurry (Omya), 15.0 grams of Nuchar SA-20 activated carbon (MeadWestvaco), and 170.0 grams of A-131 iron powder (North American Höganäs). After about 30 minutes of stirring the formulation with all ingredients, the temperature was reduced with an ice bath from about 23° C. to about 18° C. A noticeable increase in viscosity occurred when the temperature reached about 20° C. The viscosity of the formulation was measured at 2,538 cP (Brookfield Viscometer, LV-4 spindle at 100 rpm). The calculated concentration of each component of the aqueous formulation is set forth below in Table 1.

TABLE 1

Components of the Aqueous Formulation

| Component | Calculated Amount |
| --- | --- |
| Iron | 41.5% |
| Activated Carbon | 3.7% |
| SM-100 | 1.2% |
| Elite PE | 2.0% |
| Calcium Carbonate | 3.9% |
| Sodium Chloride | 3.1% |
| Water | 44.6% |

The aqueous formulation was applied to one side of the 0.9 osy fabric pieces using a #60 single wound Meyer rod. The coated pieces were dried in an oven for about 15 minutes at 110° C. The concentration of the components of the exothermic composition was then calculated from the coated and dried fabric pieces (16.4±0.4 grams), the untreated pieces of fabric (1.9±0.1 grams), and the composition of the aqueous formulation. The results are set forth below in Table 2.

TABLE 2

Components of the Exothermic Composition

| Component | Calculated Amount |
| --- | --- |
| Iron | 74.9% |
| Activated Carbon | 6.6% |
| SM-100 | 2.2% |
| Elite PE | 3.7% |
| Sodium Chloride | 5.5% |
| Calcium Carbonate | 7.1% |
| Solids Add-On Level | ~763% |

A seven-layered structure (3.5"×4") was then designed for activating the exothermic reaction. Specifically, the seven-layered structure included three of the coated fabric pieces positioned on one side of a moisture-holding layer, and the other three coated fabric pieces positioned on the other side of the moisture-holding layer. The uncoated side of the fabric pieces faced the moisture-holding layer. The total weight of the six layers of coated fabric was 15.4 grams (10.2 grams of iron). The moisture-holding layer was formed from 75 wt. % wood pulp fluff, 15 wt. % superabsorbent, and 10 wt. % of KoSa T255 bicomponent fiber. The moisture-holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543."

Prior to forming the multi-layered structure, each side of the moisture-holding layer (2.2 grams) was wetted by spraying water (6.6 grams) in an amount that increased the mass of the layer by a factor of 4.0. This seven-layered structure was then placed inside of a rectangular pouch (4"×4.5") made from a nylon spunbond microporous film laminate. The laminate was obtained from Mitsubishi International Corp. and labeled TSF EDFH 5035-TYPE. The WVTR of the laminate was measured at 455 g/m²/24 hrs by using the cup method (ASTM Standard E-96E-80). The pouch was sealed with metallized tape obtained from Nashua.

Although not specifically performed in this Example, the present inventors contemplate additional examples in which the above-referenced thermal device could employ conformable segments. For example, the pouch could contain two pieces of flat wire heat sealed within respective pockets, such as shown in FIG. 1. A suitable flat wire may be obtained from Noranda Aluminum, Inc. with the designation of Alloy 8176/EEE.

EXAMPLE 2

A thermal device was formed as described in Example 1, except that it was heat sealed in a metallized storage bag for 16 hours prior to activating the reaction. The metallized storage bag was KAL-ML5 from Kapak Corporation, a two-ply structure containing a metallized polyester layer that was adhesively laminated to a linear low density polyethylene film. The total weight of the six layers of coated fabric was 14.8 grams (9.8 grams of iron). The moisture-holding layer (2.1 grams) was wetted on both sides by spraying water (6.2 grams) in an amount that increased the mass of the layer by a factor of 3.9.

EXAMPLE 3

A coating formulation similar to that described in Example 1 was prepared and applied to one side of the 0.9 osy bonded carded web in the same manner as described in Example 1.

The calculated concentration of each component of the aqueous formulation is set forth below in Table 3.

TABLE 3

Components of the Aqueous Formulation

| Component | Calculated Amount |
|---|---|
| Iron | 38.8% |
| Activated Carbon | 3.9% |
| SM-100 | 1.3% |
| Elite PE | 2.2% |
| Calcium Carbonate | 3.9% |
| Sodium Chloride | 3.2% |
| Water | 46.7% |

The concentration of the components of the exothermic composition was calculated from the coated and dried fabric pieces (11.6±0.3 grams), the untreated pieces of fabric (1.6±0.1 grams), and the composition of the aqueous formulation. The results are set forth below in Table 4.

TABLE 4

Components of the Exothermic Composition

| Component | Calculated Amount |
|---|---|
| Iron | 72.8% |
| Activated Carbon | 7.3% |
| SM-100 | 2.4% |
| Elite PE | 4.1% |
| Sodium Chloride | 6.1% |
| Calcium Carbonate | 7.3% |
| Solids Add-On Level | ~625% |

A thermal device (3"×8") with a seven-layered structure was then designed for activating the exothermic reaction. The thermal device was heat sealed in the middle to produce a segmented device with two equal sections (3"×4"). The size of the seven-layered components that was placed in each section was 2.5"×3.5". The total weight of the six coated layers was 8.3 grams (5.2 grams of iron) for one section and 8.6 grams (5.4 grams of iron) for the other section. Further, 3.9 grams of an aqueous salt solution was applied to the moisture-holding layer of the first section and 4.0 grams of the solution was applied to the second section. The salt solution contained 9.9 wt. % sodium chloride in water, and increased the mass of the moisture holding layer of both sections by a factor of 4.0. The seven-layered structure was placed inside of a nylon spunbond microporous film laminate (described in EXAMPLE 1) pouch (segmented into two equal sections as described above) and the edges of the pouch were heat sealed. The resulting thermal device was heat sealed in a metallized storage bag for 44 hours prior to activating the reaction.

Although not specifically performed in this Example, the present inventors contemplate additional examples in which the above-referenced thermal device could employ conformable segments, such as described in Example 1.

EXAMPLE 4

A segmented thermal device was formed as described in Example 3, except that the total weight of the six coated layers was 8.2 grams (5.2 grams of iron) for one section and 8.9 grams (5.6 grams of iron) for the other section. Further, 4.1 grams and 4.0 grams of an aqueous salt solution were applied to the moisture-holding layer of the first and second sections, respectively. The salt solution contained 9.9 wt. % sodium chloride in tap water, and increased the mass of the moisture holding layer of the first and second sections by a factor of 3.9 and 3.8, respectively. The resulting thermal device was heat sealed in a metallized storage bag for 189 hours prior to activating the reaction.

EXAMPLE 5

Figure 3:
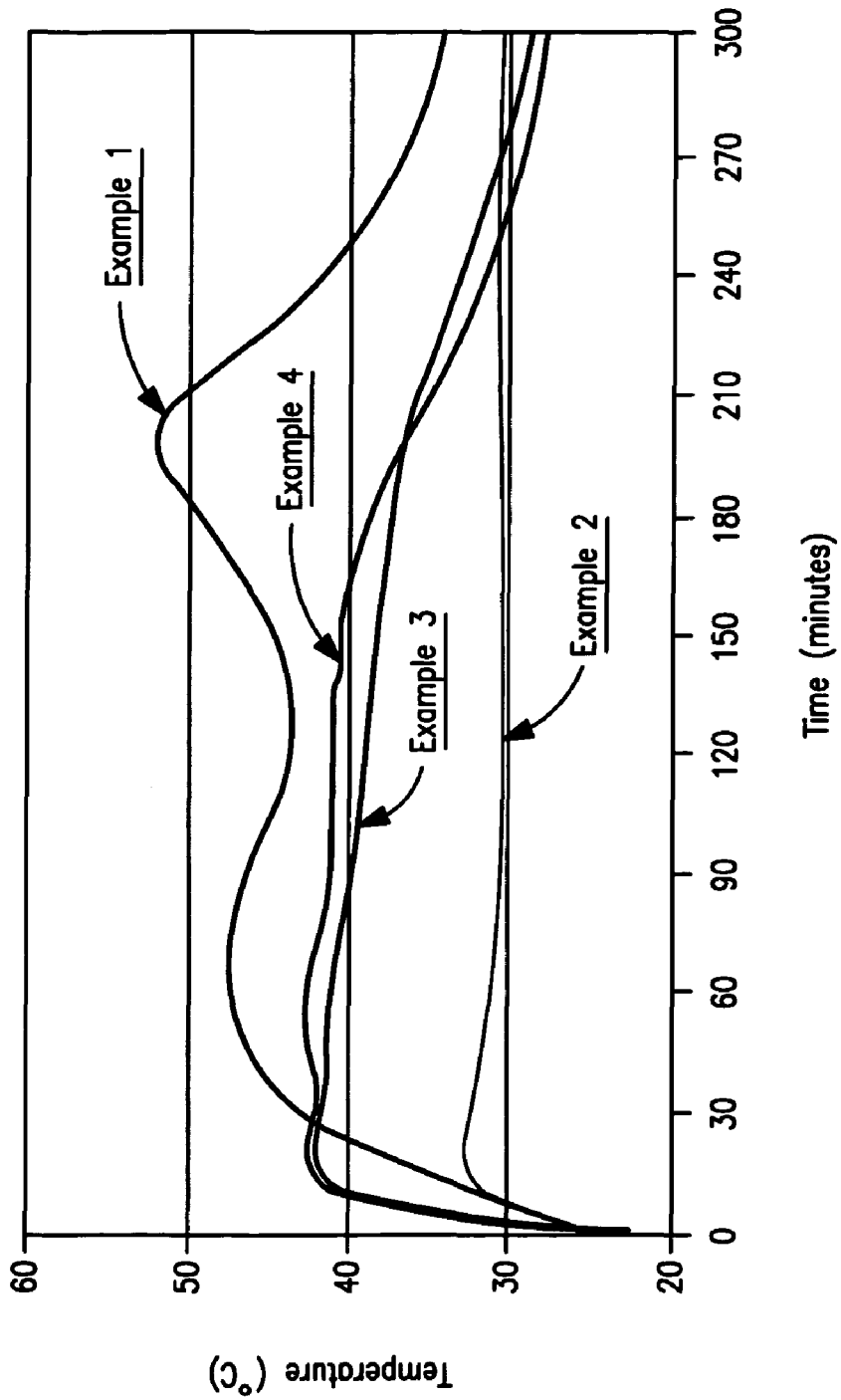
FIG. 3 is a thermal response curve showing temperature (° C.) versus time (minutes) for the samples of Examples 1-4.

The ability to achieve a controlled heating profile using a thermal device of the present invention was demonstrated. Specifically, the thermal devices of Examples 1-4 were tested. Because Example 1 was not sealed in the metallized storage bag, it was tested immediately after formation. For Examples 2-4, the metallized storage bag was opened to initiate the reaction. Testing was conducted by attaching a thermocouple wired to a data collection device to one side of the thermal device. For the segmented thermal devices described by Examples 34, both sections were tested. The temperature was recorded as a function of time (at 5 second intervals) to give the thermal response curves shown in FIG. 3. The results for only one segment of the devices described by Examples 3-4 are shown. The thermal response curve for the other segment of the Example 3 device was very similar to the first segment (1-2° C. warmer), while the other segment of the Example 4 device was about 6-8° C. warmer, most likely due to the higher iron content. As illustrated, the thermal response curves for the samples of Examples 3-4 (applied with an aqueous salt solution) reached 38° C. within about 10 minutes after opening the storage bag, and also remained from about 38 to 42° C. for at least 3 hours.

EXAMPLE 6

The ability to form a thermal device in accordance was demonstrated. A coating formulation similar to that described in Example 3 was prepared, but a higher level of sodium chloride was used. The coating formulation was applied to one side of the 0.9 osy bonded carded web in the same manner as described in Example 1. The calculated concentration of each component of the aqueous formulation is set forth below in Table 5.

TABLE 5

Components of the Aqueous Formulation

| Component | Calculated Amount |
|---|---|
| Iron | 37.3% |
| Activated Carbon | 3.7% |
| SM-100 | 1.2% |
| Elite PE | 2.3% |
| Calcium Carbonate | 3.9% |
| Sodium Chloride | 6.2% |
| Water | 45.4% |

The concentration of the components of the exothermic composition was calculated from the coated and dried fabric piece (16.3 grams), the untreated piece of fabric (1.9 grams), and the composition of the aqueous formulation. The results are set forth below in Table 6.

TABLE 6

Components of the Exothermic Composition

| Component | Calculated Amount |
|---|---|
| Iron | 68.3% |
| Activated Carbon | 6.8% |

TABLE 6-continued

Components of the Exothermic Composition

| Component | Calculated Amount |
|---|---|
| SM-100 | 2.3% |
| Elite PE | 4.1% |
| Sodium Chloride | 11.4% |
| Calcium Carbonate | 7.1% |
| Solids Add-On Level | ~758% |

A thermal device (4"×4.5") with a seven-layered structure was then designed for activating the exothermic reaction. The thermal device was formed as described in Example 1, with the size of the seven-layered components also being 3.5"×4". The total weight of the six coated layers was 15.6 grams (9.4 grams of iron). Further, each side of the moisture-holding layer (2.2 grams) was wetted by spraying 6.1 grams of water in an amount that increased the mass of the layer by a factor of 3.8. The seven-layered structure was placed inside of a nylon spunbond microporous film laminate pouch (described in Example 1) and the edges of the pouch were sealed with metallized tape, obtained from Nashua. The resulting thermal device was heat sealed in a metallized storage bag for 20 hours prior to activating the reaction.

Although not specifically performed in this Example, the present inventors contemplate additional examples in which the above-referenced thermal device could employ conformable segments, such as described above in Example 1.

EXAMPLE 7

A thermal device was formed as described in Example 1, except that a "separation layer" was used to separate the moisture-holding layer from the 3 coated layers on each side. The separation layer was a fabric/film laminate with small perforated holes for allowing vapor and gas to pass while preventing passage of liquid. It was obtained from Tredegar Film Products with the label FM-425 lot no. SHBT040060. Each side of the moisture-holding layer (2.2 grams) was wetted by spraying 6.3 grams of water in an amount that increased the mass of the layer by a factor of 3.9. Then the separation layer was placed around it with the fabric side of the separation layer in contact with the wetted moisture-holding layer. The three coated layers were then placed on each side with the uncoated side in contact with the film side of the separation layer. The total weight of the six coated layers was 14.2 grams (9.2 grams of iron). The nine-layered structure was then placed inside of a nylon spunbond microporous film laminate pouch (described in Example 1) and the edges of the pouch were sealed with metallized tape, obtained from Nashua. The resulting thermal device was heat sealed in a metallized storage bag for 20 hours prior to activating the reaction.

Although not specifically performed in this Example, the present inventors contemplate additional examples in which the above-referenced thermal device could employ conformable segments, such as described in Example 1.

EXAMPLE 8

A thermal device was formed as described in Example 7, except that the six coated layers contained a lower level of sodium chloride. The calculated concentration of each component of the aqueous formulation that was used to coat one side of the 0.9 osy bonded carded web to produce the coated layers is set forth below in Table 7.

TABLE 7

Components of the Aqueous Formulation

| Component | Calculated Amount |
|---|---|
| Iron | 42.4% |
| Activated Carbon | 3.8% |
| SM-100 | 1.2% |
| Elite PE | 2.3% |
| Calcium Carbonate | 3.9% |
| Sodium Chloride | 0.8% |
| Water | 45.6% |

The concentration of the components of the exothermic composition was then calculated from the coated and dried fabric piece (16.1 grams), the untreated piece of fabric (1.9 grams), and the composition of the aqueous formulation. The results are set forth below in Table 8.

TABLE 8

Components of the Exothermic Composition

| Component | Calculated Amount |
|---|---|
| Iron | 78.0% |
| Activated Carbon | 6.9% |
| SM-100 | 2.3% |
| Elite PE | 4.2% |
| Sodium Chloride | 1.5% |
| Calcium Carbonate | 7.2% |
| Solids Add-On Level | ~747% |

A nine-layered structure (3.5"×4") as described in Example 7 was then designed for activating the exothermic reaction. The moisture-holding layer (2.1 grams) was wetted on both sides by spraying 6.0 grams of water in an amount that increased the mass of the layer by a factor of 3.8. The total weight of the six coated layers was 15.6 grams (10.7 grams of iron). The nine-layered structure was placed inside of a nylon spunbond microporous film laminate pouch (described in Example 1) and the edges of the pouch were sealed with metallized tape, obtained from Nashua. The resulting thermal device was heat sealed in a metallized storage bag for 20 hours prior to activating the reaction.

Although not specifically performed in this Example, the present inventors contemplate additional examples in which the above-referenced thermal device could employ conformable segments, such as described in Example 1.

EXAMPLE 9

A thermal device was formed as described in Example 8, except that the moisture-holding layer contained an aqueous salt solution instead of water. Further, 6.0 grams of the aqueous salt solution was applied to the moisture-holding layer (2.2 grams) by spraying both sides, an amount that increased the mass of the layer by a factor of 3.7. The salt solution contained 10.0 wt. % sodium chloride in distilled water. The total weight of the six coated layers was 15.5 grams (10.7 grams of iron). The resulting thermal device was heat sealed in a metallized storage bag for 20 hours prior to activating the reaction.

EXAMPLE 10

The ability to achieve a controlled heating profile using a thermal device of the present invention was demonstrated. Specifically, the thermal devices of Examples 6-9 were tested. The metallized storage bag was opened to initiate the reaction. Testing was conducted by attaching a thermocouple wired to a data collection device to one side of the thermal device. The temperature was recorded as a function of time (at 5-second intervals) to give the thermal response curves shown in FIG. 4.

Figure 4:
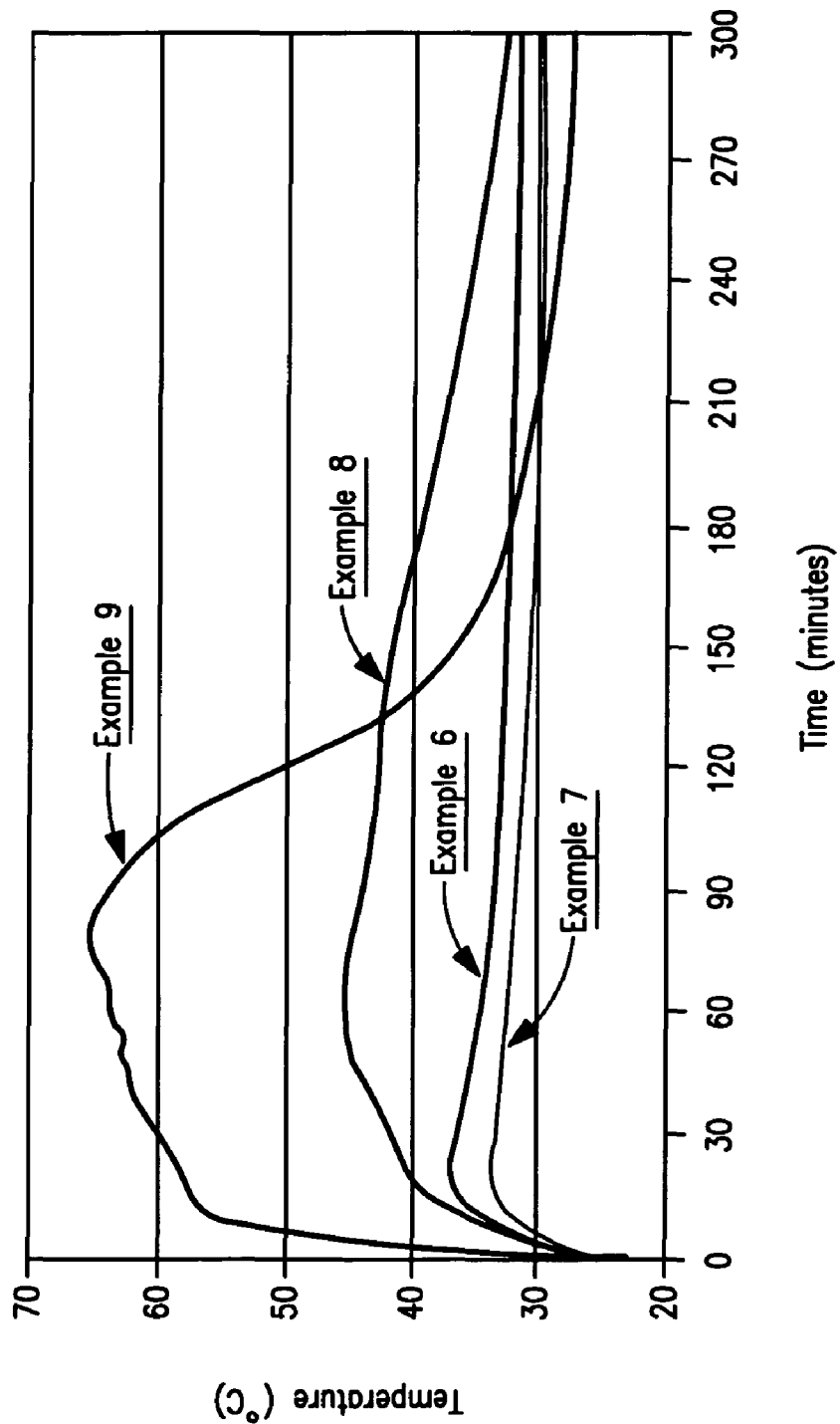
FIG. 4 is a thermal response curve showing temperature (° C.) versus time (minutes) for the samples of Examples 6-9.

As shown in FIG. 4, the sample of Example 9 (moisture-holding layer contains aqueous salt solution) provided a rapid heating rate (temperature of at least 38° C. within about 10 minutes) after opening the storage bag. The sample of Example 8 (moisture-holding layer contains water) provided a slower heating rate. However, the samples of Examples 8 and 9 that contain an exothermic composition with less salt, provided higher temperature thermal response curves compared to the samples of Examples 6 and 7 that contained higher levels of salt in the exothermic composition of the coated fabrics. Therefore, it appears that the composition of the liquid in the moisture-holding layer and the composition of the exothermic coating can be used to control the heating profile of the thermal device. More specifically, the salt content in both compositions can be adjusted to obtain the desired heating profile.

EXAMPLE 11

The ability to form a thermal device was demonstrated. A coating formulation similar to that described in Example 6 was prepared, but no sodium chloride was used. The coating formulation was applied to one side of the 0.9 osy bonded carded web in the same manner as described in Example 1. The calculated concentration of each component of the aqueous formulation is set forth below in Table 9.

TABLE 9

| Components of the Aqueous Formulation | |
| --- | --- |
| Component | Calculated Amount |
| Iron | 39.8% |
| Activated Carbon | 4.0% |
| SM-100 | 1.3% |
| Elite PE | 2.5% |
| Calcium Carbonate | 4.1% |
| Sodium Chloride | 0% |
| Water | 48.3% |

The concentration of the components of the exothermic composition was calculated from the coated and dried fabric piece (14.9 grams), the untreated piece of fabric (2.0 grams), and the composition of the aqueous formulation. The results are set forth below in Table 10.

TABLE 10

| Components of the Exothermic Composition | |
| --- | --- |
| Component | Calculated Amount |
| Iron | 77.0% |
| Activated Carbon | 7.7% |
| SM-100 | 2.6% |
| Elite PE | 4.8% |
| Sodium Chloride | 0% |
| Calcium Carbonate | 7.9% |
| Solids Add-On Level | ~645% |

A thermal device (4.25"×4.5") with a nine-layered structure was then designed for activating the exothermic reaction. The thermal device was formed as described in Example 7, with the size of the nine-layered components being 3.5"×4". The total weight of the six coated layers was 13.9 grams (9.2 grams of iron). Further, each side of the moisture-holding layer (2.4 grams) was wetted by spraying 6.7 grams of water, an amount that increased the mass of the layer by a factor of 3.8. The nine-layered structure was placed inside of a nylon spunbond microporous film laminate pouch (described in Example 1) pouch and the edges of the pouch were sealed with metallized tape, obtained from Nashua. The resulting thermal device was heat sealed in a metallized storage bag for 19.5 hours prior to activating the reaction.

Although not specifically performed in this Example, the present inventors contemplate additional examples in which the above-referenced thermal device could employ conformable segments, such as described in Example 1.

EXAMPLE 12

A thermal device was formed as described in Example 11, except that the moisture-holding layer (2.2 grams) was wetted on both sides by spraying 6.2 grams of an aqueous salt solution, an amount that increased the mass of the layer by a factor of 3.8. The salt solution contained 10 wt. % sodium chloride in distilled water. The total weight of the six coated layers was 13.7 grams (9.1 grams of iron). The resulting thermal device was heat sealed in a metallized storage bag for 19.5 hours prior to activating the reaction.

EXAMPLE 13

A thermal device was formed as described in Example 7, except that the moisture-holding layer (2.2 grams) was wetted on both sides by spraying 6.0 grams of an aqueous salt solution, an amount that increased the mass of the layer by a factor of 3.7. The salt solution contain 10 wt. % sodium chloride in distilled water. The thermal device was also slightly larger than Example 7 at 4.25"×4.5". The total weight of the six coated layers was 14.6 grams (9.6 grams of iron). The nine-layered structure was then placed inside of a nylon spunbond microporous film laminate pouch (described in Example 1) and the edges of the pouch were sealed with metallized tape, obtained from Nashua. The resulting thermal device was heat sealed in a metallized storage bag for 18 hours prior to activating the reaction.

Although not specifically performed in this Example, the present inventors contemplate additional examples in which the above-referenced thermal device could employ conformable segments, such as described in Example 1.

EXAMPLE 14

A thermal device was formed as described in Example 9. Further, the moisture-holding layer (2.2 grams) was wetted on both sides by spraying 6.1 grams of an aqueous salt solution, an amount that increased the mass of the layer by a factor of 3.8. The salt solution contained 10.0 wt. % sodium chloride in distilled water. The total weight of the six coated layers was 16.6 grams (11.4 grams of iron). The resulting thermal device was heat sealed in a metallized storage bag for 18 hours prior to activating the reaction.

EXAMPLE 15

Figure 5:
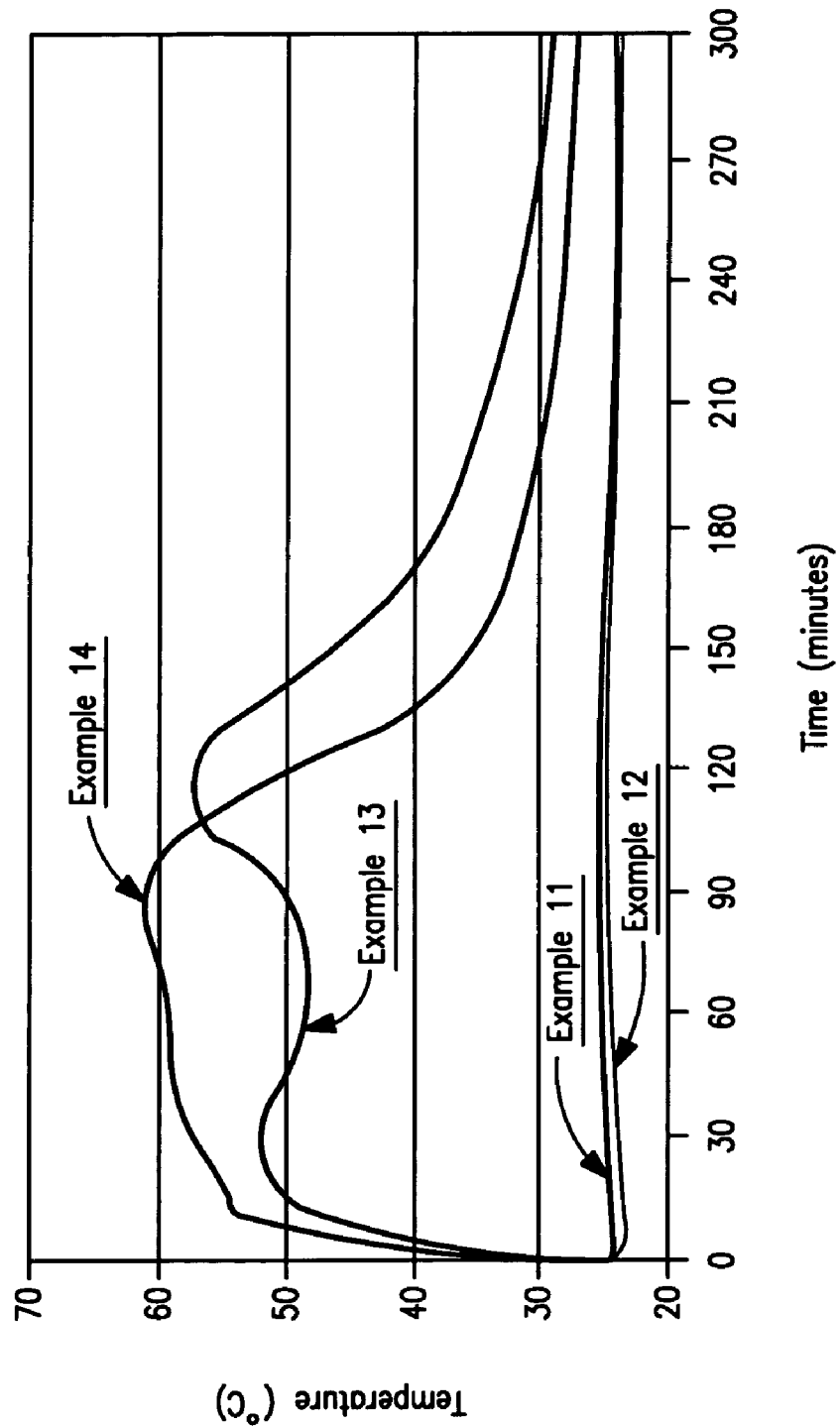
FIG. 5 is a thermal response curve showing temperature (° C.) versus time (minutes) for the samples of Examples 11-14.

The ability to achieve a controlled heating profile using a thermal device of the present invention was demonstrated. Specifically, the thermal devices of Examples 11-14 were tested. The metallized storage bag was opened to initiate the reaction. Testing was conducted by attaching a thermocouple wired to a data collection device to one side of the thermal device. The temperature was recorded as a function of time (at 5-second intervals) to give the thermal curves shown in FIG. 5.

EXAMPLE 16

The ability to form a thermal device was demonstrated. Initially, a 7"-wide roll of a bonded carded web fabric was provided that had a basis weight of 1.5 ounces per square yard (50 grams per square meter). The fabric was formed from a blend of 60 wt. % bicomponent fibers and 40 wt. % polyester fibers. The bicomponent fibers were obtained from FiberVisions, Inc. of Covington, Ga. under the name "ESC 215", which had a polyethylene sheath and polypropylene core, a denier of 1.5, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 1-gallon metal pail, 34.5 grams of METOLOSE SM-100 (Shin-Etsu Chemical Co., Ltd.) and 25.0 grams of sodium chloride (Mallinckrodt) were added to 1172.0 grams of distilled water that was stirred and heated to 68° C. The mixture was stirred and allowed to cool as the following additional ingredients were added sequentially: 139.6 grams of DUR-O-SET® Elite PE 25-220A ethylene-vinyl acetate emulsion (Celanese Emulsions), 330.2 grams of XP-5200-6 sample #05.2435503 calcium carbonate slurry (Omya), 60.1 grams of Nuchar SA-400 activated carbon (MeadWestvaco), and 1181.1 grams of A-131 iron powder (North American Höganäs). After about 30 minutes of stirring the formulation with all ingredients, the temperature was reduced with an ice bath to about 10° C. A noticeable increase in viscosity occurred when the temperature was reduced. The calculated concentration of each component of the aqueous formulation is set forth below in Table 11.

TABLE 11

Components of the Aqueous Formulation

| Component | Calculated Amount |
|---|---|
| Iron | 40.1% |
| Activated Carbon | 2.0% |
| SM-100 | 1.2% |
| Elite PE | 2.3% |
| Calcium Carbonate | 3.8% |
| Sodium Chloride | 0.8% |
| Water | 49.8% |

The aqueous formulation was applied to one side of the 1.5 osy fabric in a pilot line process using a knife coater. The gap between the knife and steel roller that carried the fabric was set at 900 micron. The line speed was 0.25 meters per minute. The pilot line coater contained a four-foot drier set at 145° C. that was used to partially dry the coated fabric. The partially dried coated fabric was cut into 17-inch pieces and placed in a laboratory oven at 110° C. for about 20 minutes to complete the drying step. The concentration of the components of the exothermic composition was calculated from the coated and dried fabric pieces (56.5±1.5 grams), the untreated piece of fabric (4.3 grams), and the composition of the aqueous formulation. The results are set forth below in Table 12.

TABLE 12

Components of the Exothermic Composition

| Component | Calculated Amount |
|---|---|
| Iron | 79.7% |
| Activated Carbon | 4.0% |
| SM-100 | 2.3% |
| Elite PE | 4.6% |
| Sodium Chloride | 1.7% |
| Calcium Carbonate | 7.6% |
| Solids Add-On Level | ~1214% |

A five-layered structure (1.6"×8") was then designed for activating the exothermic reaction. Specifically, the five-layered structure included one of the coated fabric pieces positioned on one side of a moisture-holding layer, and another coated fabric piece positioned on the other side of the moisture-holding layer. The uncoated side of the fabric pieces faced the moisture-holding layer. The moisture-holding layer was formed from 90 wt. % wood pulp fluff (Weyerhaeuser NF401) and 10 wt. % of KoSa T255 bicomponent fiber. The moisture-holding layer had a basis weight of 175 grams per square meter and a density of 0.08 grams per cubic centimeter. A "separation layer" was used to separate the moisture-holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture-holding layer (1.5 grams) was wetted on each side by spraying 4.2 grams of distilled water, an amount that increased the mass of the layer by a factor of 3.8. Then the separation layer was placed around it with the fabric side of the separation layer in contact with the wetted moisture-holding layer. A coated layer was then placed on each side with the uncoated side in contact with the film side of the separation layer. The total weight of the two coated layers was 13.5 grams (9.9 grams of iron). The five-layered structure was then placed inside of a pouch (3"×9") that was sealed with a heat sealer. The pouch was made from a nylon spunbond microporous film laminate (described in Example 1) that had a layer of stapleknit fabric heat sealed to the nylon spunbond side. The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.).

The pouch was made by folding a 6"×9" piece of the materials described above in half to produce the 3"×9" size. A flat wire that measured approximately 8.5 inches (21.59 centimeters) in length, 0.1 inch (2.4 millimeters) in width, and 0.01 inch (0.24 millimeters) in thickness was then placed inside of and against the fold. The wire was obtained from Noranda Aluminum, Inc. with the designation of Alloy 8176/EEE. A pocket approximately 0.375 inch (9.525 millimeters) in width and 9 inches (22.86 centimeters) in length was formed around the wire by heat sealing the top to the bottom of the pouch. A second flat wire with the same characteristics as the first wire was then placed at the other edge of the pouch. A second pocket approximately 0.375 inch (9.525 millimeters) in width and 9 inches (22.86 centimeters) in length was formed around this second wire by heat sealing the top to the bottom of the pouch along the outer edge and at 0.375 inch (9.525 millimeters) from the outer edge.

EXAMPLE 17

A thermal device was formed as described in Example 16, except that the moisture-holding layer contained an aqueous salt solution instead of tap water. Further, 4.3 grams of the aqueous salt solution was applied to the moisture-holding layer (1.5 grams), an amount that increased the mass of the layer by a factor of 3.8. The salt solution contained 10.0 wt. % sodium chloride in distilled water. The total weight of the two coated layers was 13.7 grams (10.1 grams of iron). The resulting thermal device was heat sealed in a metallized storage bag for 8 days prior to activating the reaction.

EXAMPLE 18

A thermal device was formed as described in Example 16, except the moisture-holding layer was formed from 75 wt. % wood pulp fluff (Weyerhaeuser NB416), 15 wt. % superabsorbent (Degussa SXM9543), and 10 wt. % of KoSa T255 bicomponent fiber, and had a basis weight of 225 grams per square meter and a density of 0.12 grams per cubic centimeter. The moisture-holding layer also contained an aqueous salt solution instead of tap water; 5.8 grams of the aqueous salt solution was applied to the moisture-holding layer (2.2 grams), an amount that increased the mass of the layer by a factor of 3.7. The salt solution contained 10.0 wt. % sodium chloride in distilled water. The total weight of the two coated layers was 14.6 grams (10.7 grams of iron). The resulting thermal device was heat sealed in a metallized storage bag for 66 hours prior to activating the reaction.

EXAMPLE 19

A thermal device was formed as described in Example 16, except the moisture-holding layer was formed from the material described in Example 18. The moisture-holding layer also contained an aqueous salt solution instead of tap water; 6.0 grams of the aqueous salt solution was applied to the moisture-holding layer (2.1 grams), an amount that increased the mass of the layer by a factor of 3.8. The salt solution contained 10.0 wt. % sodium chloride in distilled water. The total weight of the two coated layers was 14.7 grams (10.8 grams of iron). The resulting thermal device was heat sealed in a metallized storage bag for 66 hours prior to activating the reaction.

EXAMPLE 20

The ability to achieve a controlled heating profile using a thermal device of the present invention was demonstrated. Specifically, the thermal devices of Examples 16-19 were tested. The metallized storage bag was opened to initiate the reaction. Testing was conducted by attaching a thermocouple wired to a data collection device to one side of the thermal device. The temperature was recorded as a function of time (at 5-second intervals) to give the thermal curves shown in FIG. 6.

Figure 6:
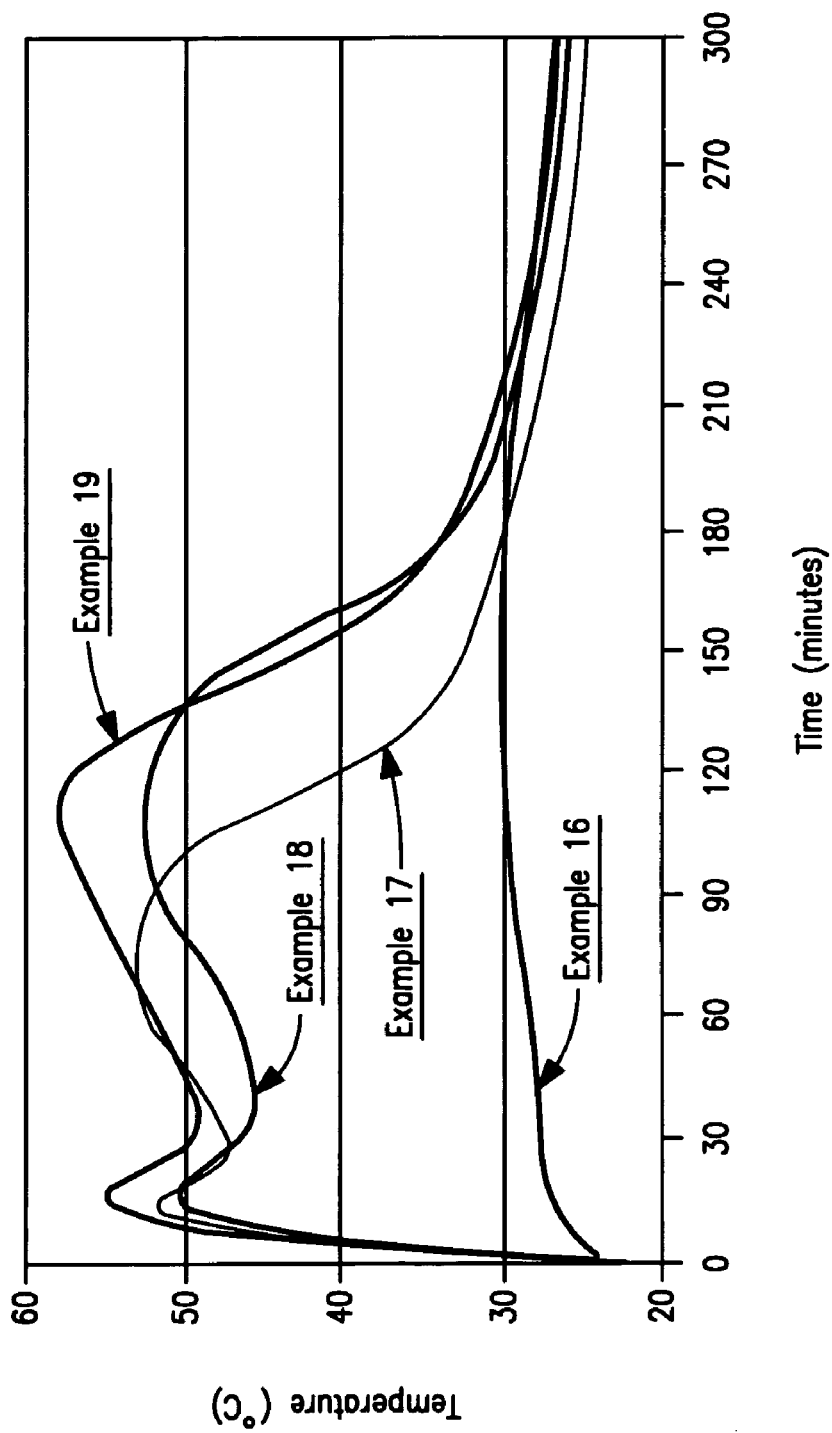
FIG. 6 is a thermal response curve showing temperature (° C.) versus time (minutes) for the samples of Examples 16-19.

As shown in FIG. 6, the thermal response curves for the samples of Examples 17-19 did show a rapid heating rate (temperature of at least 38° C. within about 10 minutes) and an elevated temperature profile for an extended period of time. These samples contained salt both in the exothermic composition and in the liquid held by the moisture-holding layer. Furthermore, a moisture-holding layer that did not contain superabsorbent was used for the sample of Example 17, and the thermal response curve was similar to the curves for the samples of Examples 18 and 19. Note in FIG. 6 that the thermal response curve for the sample of Example 16 did not show a rapid heating rate and the temperature only reached about 30° C. This sample only contained water in the moisture-holding layer.

EXAMPLE 21

The ability to form a thermal device in accordance was demonstrated. The coated fabric described in Example 16 was used in a five-layered structure (2.5"×7") for activating the exothermic reaction. Specifically, the five-layered structure included one of the coated fabric pieces positioned on one side of a moisture-holding layer, and another coated fabric piece positioned on the other side of the moisture-holding layer. The uncoated side of the fabric pieces faced the moisture-holding layer. The moisture-holding layer was formed from 75 wt. % wood pulp fluff, 15 wt. % superabsorbent, and 10 wt. % of KoSa T255 bicomponent fiber. The moisture-holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543." A "separation layer" was used to separate the moisture-holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture-holding layer (2.7 grams) was wetted on each side by spraying 7.6 grams of an aqueous salt solution, an amount that increased the mass of the layer by a factor of 3.8. The salt solution contained 3.0 wt. % sodium chloride in distilled water. Then the separation layer was placed around it with the fabric side of the separation layer in contact with the wetted moisture holding layer. A coated layer was then placed on each side with the uncoated side in contact with the film side of the separation layer. The total weight of the two coated layers was 18.1 grams (13.3 grams of iron). The five-layered structure was then placed inside of a pouch (3.2"×8") that was sealed with a heat sealer. The pouch was made from a nylon spunbond microporous film laminate (described in Example 1) that had a layer of stapleknit fabric heat sealed to the nylon spunbond side. The stapleknit fabric was produced from 20% wood pulp fluff (50% Northern softwood kraft fibers/50% Alabama Pine bleached kraft softwood fibers), 58% 1.5 denier polyester fiber (Invista Type 103), and 22% polypropylene spunbond (Kimberly-Clark Corp.). The resulting thermal device was heat sealed in a metallized storage bag for 64 hours prior to activating the reaction.

Although not specifically performed in this Example, the present inventors contemplate additional examples in which the above-referenced thermal device could employ conformable segments, such as described in Example 1.

EXAMPLE 22

A thermal device was formed as described in Example 21. The moisture-holding layer (2.7 grams) contained 7.2 grams of an aqueous salt solution, an amount that increased the mass of the layer by a factor of 3.7. The salt solution contained 3.0 wt. % sodium chloride in distilled water. The total weight of the two coated layers was 17.1 grams (12.5 grams of iron). The resulting thermal device was heat sealed in a metallized storage bag for 64 hours prior to activating the reaction.

EXAMPLE 23

A thermal device was formed as described in Example 21. The moisture holding layer (2.7 grams) contained 7.6 grams of an aqueous salt solution, an amount that increased the mass of the layer by a factor of 3.8. The salt solution contained 3.0 wt. % sodium chloride in distilled water. The total weight of the two coated layers was 17.3 grams (12.6 grams of iron). The resulting thermal device was heat sealed in a metallized storage bag for 64 hours prior to activating the reaction.

EXAMPLE 24

A thermal device was formed as described in Example 21. The moisture holding layer (2.7 grams) contained 7.2 grams of an aqueous salt solution, an amount that increased the mass of the layer by a factor of 3.7. The salt solution contained 3.0 wt. % sodium chloride in distilled water. The total weight of the two coated layers was 18.0 grams (13.2 grams of iron). The resulting thermal device was heat sealed in a metallized storage bag for 64 hours prior to activating the reaction.

EXAMPLE 25

Figure 7:
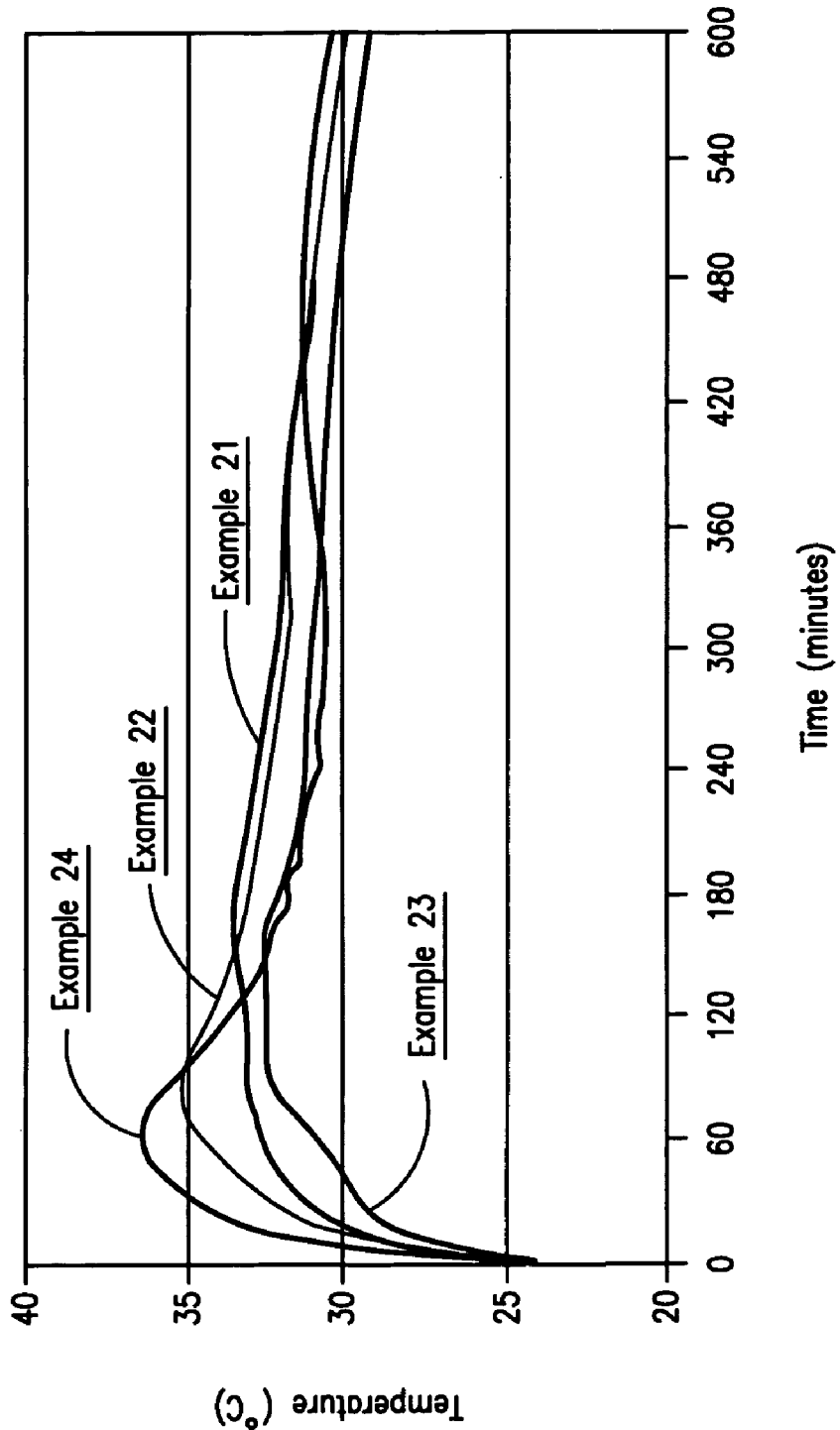
FIG. 7 is a thermal response curve showing temperature (° C.) versus time (minutes) for the samples of Examples 21-24.

The ability to achieve a controlled heating profile using a thermal device of the present invention was demonstrated. Specifically, the thermal devices of Examples 21-24 were tested. The metallized storage bag was opened to initiate the reaction. Testing was conducted by attaching a thermocouple wired to a data collection device to one side of the thermal device. The temperature was recorded as a function of time (at 5-second intervals) to give the thermal curves shown in FIG. 7. Note that the thermal response curves for the samples of Examples 21-24 are lower in temperature but last longer than those for the samples of Examples 18 and 19 (FIG. 6). Therefore, the amount of salt in the liquid held by the moisture-holding layer can be used to control the thermal response curve.

EXAMPLE 26

The breathability of the pouch was measured for Examples 6-9 and 11-14 to verify that the large difference in the thermal response curves (FIGS. 4 and 5) was not due to variability in pouch breathability. The pouch for these Examples was a nylon spunbond microporous film laminate obtained from Mitsubishi International Corp. and labeled TSF EDFH 5035-TYPE. The WVTR of the laminate was measured at 455±14 g/m²/24 hrs (10 samples) using the cup method (ASTM Standard E-96E-80). This same method was used to measure the WVTR for the pouches of Examples 6-9 and 11-14 after the exothermic reaction was completed. The results are shown in Table 13.

TABLE 13

Breathability (WVTR) for Pouches of Examples 6–9 & 11–14

| Example | Top of Pouch (g/m²/24 hrs) | Bottom of Pouch (g/m²/24 hrs) |
|---|---|---|
| 6 | 430 | 443 |
| 7 | 433 | 416 |
| 8 | 414 | 430 |
| 9 | 416 | 438 |
| 11 | 449 | 424 |
| 12 | 424 | 424 |
| 13 | 416 | 449 |
| 14 | 424 | 419 |

The data shown in Table 13 verifies that the pouches used for the thermal devices of Examples 6-9 and 11-14 were consistent in breathability. Therefore, the large differences in the thermal response curves for these thermal devices may be attributed to the liquid applied to the moisture-holding layer (water or 10% sodium chloride in water) and/or the composition of the exothermic coating (i.e. amount of salt).

EXAMPLE 27

The ability to control the delivery of moisture by a moisture-holding layer for use in the thermal device of the present invention was demonstrated. Four (4) different samples were tested. Samples A and B were formed from an airlaid web that contained 75 wt. % wood pulp fluff (Weyerhaeuser NB416), 15 wt. % superabsorbent, and 10 wt. % of "T255" PE/PP bicomponent fibers (KoSa). The airlaid web had a basis weight of 225 grams per square meter and a density of 0.12 grams per cubic centimeter. Samples C and D were formed from an airlaid web that contained 90 wt. % wood pulp fluff (Weyerhaeuser NF405) and 10 wt. % of "T255" PE/PP bicomponent fibers (KoSa). The airlaid web had a basis weight of 175 grams per square meter and a density of 0.08 grams per cubic centimeter. The superabsorbent was obtained from Degussa AG under the name "SXM 9543."

Figure 8:
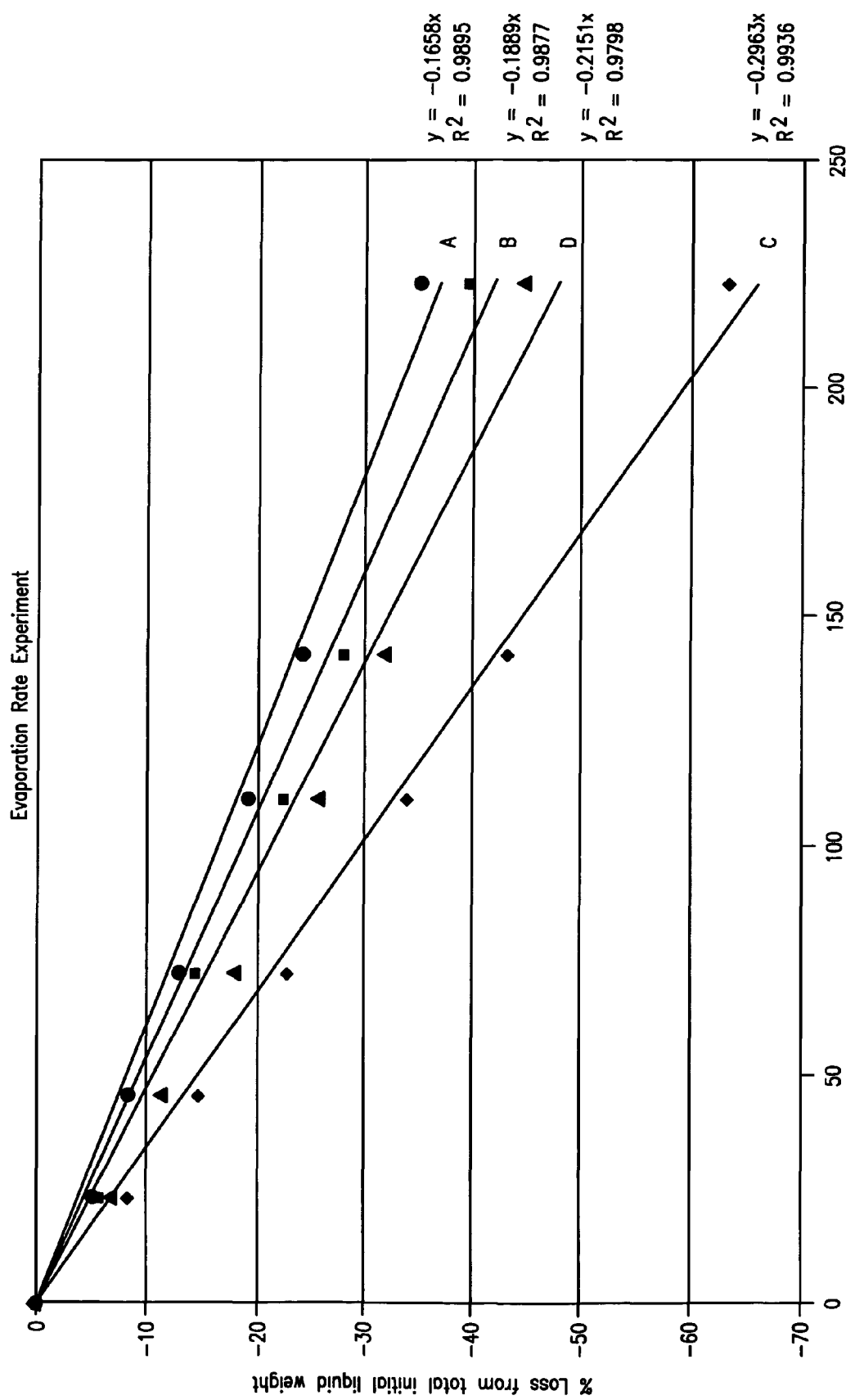
FIG. 8 is an evaporation curve showing the loss of liquid weight (%) versus time (minutes) for the moisture-holding layers of Example 27.

Each airlaid substrate was cut to a size of 3.5 inches by 4.0 inches and sprayed on each side with an aqueous solution such that the wet weight was about 3.7 to 4.0 times higher than the dry weight. For Samples A and C, the aqueous solution contained only distilled water. For Samples B and D, the aqueous solution contained 10 wt. % sodium chloride in distilled water. The wet substrates were placed on balances located within an environmental chamber. The humidity and temperature within the chamber were then recorded as a function of time. In addition, the weight of each wet substrate was also recorded to obtain the "percent moisture loss" as a function of time. The "percent moisture loss" was calculated by subtracting the measured wet weight from the original wet weight, dividing this value by the original wet weight, and then multiplying by 100. The resulting evaporation curves are shown in FIG. 8. Note that Sample B (SAP/Saline) delivered more moisture as a function of time (i.e. higher evaporation rate) compared to Sample A (SAP/Water). Also, Sample D (No SAP/Saline) had a moisture delivery rate slightly higher than Sample B, but much less than Sample C (No SAP/Water).

EXAMPLE 28

The ability to form a thermal device was demonstrated. Initially, a 7"-wide roll of a dual layer bonded carded web was provided. One side of the web contained 0.5 osy of a 100% 1.5 denier FiberVisions ESC 215 bicomponent (PE sheath/PP core) fiber with 0.55% HR6 finish. The other side of the web contained 1.75 osy of a blend of 40% 15 denier Invista T-295 polyester fiber with 0.50% L1 finish and 60% of a 28 denier FiberVisions ESC bicomponent (PE sheath/PP core) fiber with 0.55% HR6 finish. Therefore, the total basis weight of the dual layer bonded carded web was 2.25 osy.

An aqueous coating formulation was prepared as follows. In a 1-gallon metal pail, 34.5 grams of METOLOSE SM-100 (Shin-Etsu Chemical Co., Ltd.) and 87.0 grams of sodium chloride (Mallinckrodt) were added to 1172.1 grams of distilled water that was stirred and heated to 68° C. The mixture was stirred and allowed to cool as the following additional ingredients were added sequentially: 139.1 grams of DUR-O-SET® Elite PE 25-220A ethylene-vinyl acetate emulsion (Celanese Emulsions), 330.8 grams of XP-5200-6 sample #05.2435503 calcium carbonate slurry (Omya), 72.0 grams of Nuchar SA-400 activated carbon (MeadWestvaco), and 1181.0 grams of A-131 iron powder (North American Höganäs). After about 30 minutes of stirring the formulation with all ingredients, the temperature was reduced with an ice bath to about 15° C. A noticeable increase in viscosity occurred when the temperature was reduced. Finally, the temperature of the formulation was increased with a hot water bath to 22° C. prior to coating the bonded carded web. The calculated concentration of each component of the aqueous formulation is set forth below in Table 14.

TABLE 14

Components of the Aqueous Formulation

| Component | Calculated Amount |
|---|---|
| Iron | 39.2% |
| Activated Carbon | 2.4% |
| SM-100 | 1.1% |
| Elite PE | 2.2% |
| Calcium Carbonate | 3.8% |
| Sodium Chloride | 2.9% |
| Water | 48.4% |

The aqueous formulation was applied to the polyester/bicomponent fiber side of the dual layer bonded carded web in a pilot line process using a knife coater. The gap between the knife and steel roller that carried the fabric was set at 900 micron. The line speed was 0.25 meters per minute. The pilot line coater contained a four-foot drier set at 145° C. that was used to partially dry the coated fabric. The partially dried coated fabric was cut into 17-inch pieces and placed in a laboratory oven at 110° C. for about 20 minutes to complete the drying step. The concentration of the components of the exothermic composition was calculated from the coated and dried fabric pieces (53.8±2.7 grams), the untreated piece of fabric (4.3 grams), and the composition of the aqueous formulation. The results are set forth below in Table 15.

TABLE 15

Components of the Exothermic Composition

| Component | Calculated Amount |
|---|---|
| Iron | 75.9% |
| Activated Carbon | 4.6% |
| SM-100 | 2.2% |
| Elite PE | 4.3% |
| Sodium Chloride | 5.6% |
| Calcium Carbonate | 7.3% |
| Solids Add-On Level | ~1151% |

A five-layered structure (1.6"×8") was then designed for activating the exothermic reaction. Specifically, the five-layered structure included one of the coated fabric pieces positioned on one side of a moisture-holding layer, and another coated fabric piece positioned on the other side of the moisture-holding layer. The uncoated side of the fabric pieces faced the moisture-holding layer. The moisture-holding layer was formed from 75 wt. % wood pulp fluff, 15 wt. % superabsorbent, and 10 wt. % of KoSa T255 bicomponent fiber. The moisture-holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543."

A "separation layer" was used to separate the moisture-holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture-holding layer (2.0 grams) was wetted on each side by spraying 5.8 grams of an aqueous salt solution, an amount that increased the mass of the layer by a factor of 3.9. The salt solution contained 10.0 wt. % sodium chloride in distilled water. Then the separation layer was placed around it with the fabric side of the separation layer in contact with the wetted moisture-holding layer. A coated layer was then placed on each side with the uncoated side in contact with the film side of the separation layer. The total weight of the two coated layers was 13.1 grams (9.1 grams of iron). The five-layered structure was then placed inside of a pouch (3"×9") that was sealed with a heat sealer. The pouch was made from a nylon spunbond microporous film laminate (described in Example 1) that had a layer of stapleknit fabric heat sealed to the nylon spunbond side. The stapleknit fabric was produced from 20% wood pulp fluff (50% Northern softwood kraft fibers/50% Alabama Pine bleached kraft softwood), 58% 1.5 denier polyester fiber (Invista Type 103), and 22% polypropylene spunbond (Kimberly-Clark Corp.).

The pouch was made by folding a 6"×9" piece of the materials described above in half to produce the 3"×9" size. A flat wire that measured approximately 8.5 inches (21.59 centimeters) in length, 0.1 inch (2.4 millimeters) in width, and 0.01 inch (0.24 millimeters) in thickness was then placed inside of and against the fold. The wire was obtained from Noranda Aluminum, Inc. with the designation of Alloy 8176/EEE. A pocket approximately 0.375 inch (9.525 millimeters) in width and 9 inches (22.86 centimeters) in length was formed around the wire by heat sealing the top to the bottom of the pouch. A second flat wire with the same characteristics as the first wire was then placed at the other edge of the pouch. A second pocket approximately 0.375 inch (9.525 millimeters) in width and 9 inches (22.86 centimeters) in length was formed around this second wire by heat sealing the top to the bottom of the pouch along the outer edge and at 0.375 inch (9.525 millimeters) from the outer edge.

The resulting thermal device was heat sealed in a metallized storage bag for about 67 hours prior to activating the reaction.

EXAMPLE 29

A thermal device was formed as described in Example 28. The moisture-holding layer (2.1 grams) contained 5.8 grams of an aqueous salt solution, an amount that increased the mass of the layer by a factor of 3.8. The salt solution contained 10.0 wt. % sodium chloride in distilled water. The total weight of the two coated layers was 14.4 grams (10.0 grams of iron). The resulting thermal device was heat sealed in a metallized storage bag for about 67 hours prior to activating the reaction.

EXAMPLE 30

A thermal device was formed as described in Example 28. The moisture-holding layer (2.2 grams) contained 5.8 grams of an aqueous salt solution, an amount that increased the mass of the layer by a factor of 3.7. The salt solution contained 10.0 wt. % sodium chloride in distilled water. The total weight of the two coated layers was 12.1 grams (8.4 grams of iron). The resulting thermal device was heat sealed in a metallized storage bag for 1 day prior to activating the reaction.

EXAMPLE 31

A thermal device was formed as described in Example 28. The moisture-holding layer (2.2 grams) contained 5.9 grams of an aqueous salt solution, an amount that increased the mass of the layer by a factor of 3.7. The salt solution contained 10.0 wt. % sodium chloride in distilled water. The total weight of the two coated layers was 11.6 grams (8.1 grams of iron). The resulting thermal device was heat sealed in a metallized storage bag for 1 day prior to activating the reaction.

EXAMPLE 32

The ability to achieve a controlled heating profile using a thermal device of the present invention was demonstrated. Specifically, the thermal devices of Examples 28-31 were tested. The metallized storage bag was opened to initiate the reaction. Testing was conducted by attaching a thermocouple wired to a data collection device to one side of the thermal device. The temperature was recorded as a function of time (at 5-second intervals) to give the thermal curves shown in FIG. 9.

Figure 9:
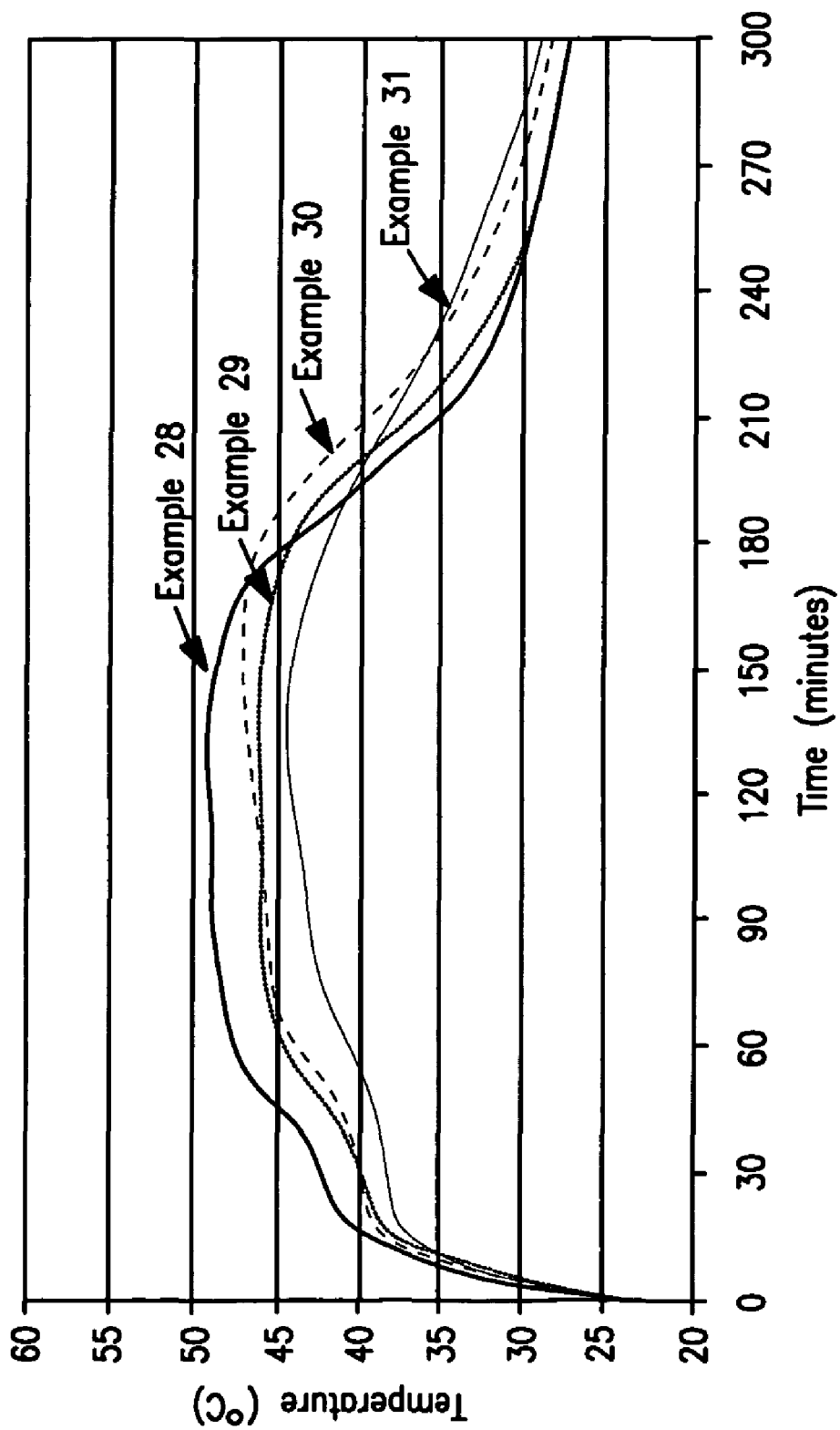
FIG. 9 is an evaporation curve showing the loss of liquid weight (%) versus time (minutes) for the moisture-holding layers of Example 32.

As shown in FIG. 9, the thermal response curves for the samples of Examples 28-31 did show a rapid heating rate (temperature of at least 38° C. within about 10 minutes) and an elevated temperature profile for an extended period of time.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A chemically activated thermal device that comprises an exothermic composition positioned within an enclosure and multiple conformable segments positioned within at least two pockets, wherein a first pocket is peripherally located on a first side of the enclosure and a second pocket is peripherally located on a second side of the enclosure, wherein the conformable segments are malleable and have an aspect ratio of from about 20 to about 400, wherein the enclosure and the first pocket are bonded together at a seal and wherein the enclosure and the second pocket are bonded together at a seal so that the exothermic composition is constrained within the enclosure and the conformable segments are moveably constrained within the pockets.

2. The thermal device of claim 1, wherein the conformable segments contain a metal or an alloy thereof.

3. The thermal device of claim 2, wherein the metal is aluminum.

4. The thermal device of claim 1, wherein the aspect ratio of the conformable segments is from about 40 to about 200.

5. The thermal device of claim 1, wherein the conformable segments have a length dimension of from about 5 to about 100 centimeters.

6. The thermal device of claim 1, wherein the conformable segments have a width dimension of from about 0.1 to about 20 millimeters.

7. The thermal device of claim 1, wherein the thermal device comprises from 5 to 15 conformable segments.

8. The thermal device of claim 1, wherein the thermal device comprises from 2 to 100 conformable segments.

9. The thermal device of claim 1, wherein the length dimension of the conformable segments is substantially parallel to the length dimension of the thermal device.

10. The thermal device of claim 1, wherein the ratio of the width of the pocket to the width of the conformable segments is from about 1.0 to about 10.0.

11. The thermal device of claim 1, wherein the ratio of the width of the pockets to the width of the conformable segments is from about 2.0 to about 5.0.

12. The thermal device of claim 1, wherein the pocket are located adjacent to the periphery of the thermal device.

13. The thermal device of claim 1, further comprising an outer cover that is bonded together to form the pockets.

14. The thermal device of claim 13, wherein the outer cover comprises a breathable material.

15. The thermal device of claim 1, wherein the exothermic composition comprises an oxidizable metal that undergoes an exothermic reaction upon exposure to oxygen and moisture.

16. The thermal device of claim 15, wherein the exothermic composition further comprises a carbon component, binder, and electrolytic salt.

17. The thermal device of claim 16, wherein the exothermic composition is coated onto a thermal substrate.

18. The thermal device of claim 1, wherein the exothermic composition is coated onto a thermal substrate.

19. The thermal device of claim 1, wherein the conformable segments are able to move independently.

20. A package comprising a chemically activated thermal device that comprises an exothermic composition positioned within an enclosure and multiple conformable segments positioned within at least two pockets, wherein a first pocket is peripherally located on a first side of the enclosure and a second pocket is peripherally located on a second side of the enclosure, wherein the conformable segments are malleable and have an aspect ratio of from about 20 to about 400, wherein the enclosure and the first pocket are bonded together at a seal and wherein the enclosure and the second pocket are bonded together at a seal so that the exothermic composition is constrained within the enclosure and the conformable segments are moveably constrained within the pockets, wherein the enclosure inhibits the passage of oxygen, moisture, or both to the exothermic composition.

21. A method for providing heat to a body part, the method comprising placing a thermal device adjacent to the body part and conforming the device to the shape of the body part, wherein the thermal device comprises an exothermic composition positioned within an enclosure and multiple conformable segments positioned within at least two pockets, wherein a first pocket is peripherally located on a first side of the enclosure and a second pocket is peripherally located on a second side of the enclosure, wherein the conformable segments are malleable and have an aspect ratio of from about 20 to about 400, wherein the enclosure and the first pocket are bonded together at a seal and wherein the enclosure and the second pocket are bonded together at a seal-so that the exothermic composition is constrained within the enclosure and the conformable segments are moveably constrained within the pockets.

* * * * *

UNITED STATES PATENT AND TRADEMARK OFFICE
CERTIFICATE OF CORRECTION

| | |
|---|---|
| PATENT NO. | : 8,137,392 B2 |
| APPLICATION NO. | : 11/474079 |
| DATED | : March 20, 2012 |
| INVENTOR(S) | : Joshua Friedensohn et al. |

Page 1 of 1

It is certified that error appears in the above-identified patent and that said Letters Patent is hereby corrected as shown below:

Column 40, line 10 (Claim 12) "..wherein the pocket are..." should read
--...wherein the pockets are...--

Signed and Sealed this
Eleventh Day of December, 2012

David J. Kappos
*Director of the United States Patent and Trademark Office*